United States Patent
Muotri et al.

(10) Patent No.: US 9,340,775 B2
(45) Date of Patent: May 17, 2016

(54) INDUCED PLURIPOTENT STEM CELL PRODUCED BY TRANSFECTING A HUMAN NEURAL STEM CELL WITH AN EPISOMAL VECTOR ENCODING THE OCT4 AND NANOG PROTEINS

(75) Inventors: Alysson R. Muotri, La Jolla, CA (US); Fred H. Gage, La Jolla, CA (US); Maria C. N. Marchetto, La Jolla, CA (US)

(73) Assignee: THE SALK INSTITUTE FOR BIOLOGICAL STUDIES, La Jolla, CA (US)

( * ) Notice: Subject to any disclaimer, the term of this patent is extended or adjusted under 35 U.S.C. 154(b) by 638 days.

(21) Appl. No.: 13/259,668

(22) PCT Filed: Mar. 24, 2010

(86) PCT No.: PCT/US2010/028524
§ 371 (c)(1),
(2), (4) Date: Jan. 10, 2012

(87) PCT Pub. No.: WO2010/111409
PCT Pub. Date: Sep. 30, 2010

(65) Prior Publication Data
US 2012/0107286 A1 May 3, 2012

Related U.S. Application Data

(60) Provisional application No. 61/163,379, filed on Mar. 25, 2009.

(51) Int. Cl.
| | | |
|---|---|---|
| *C12N 5/00* | (2006.01) | |
| *C12N 15/00* | (2006.01) | |
| *C12N 5/074* | (2010.01) | |
| *C12N 15/79* | (2006.01) | |
| *C12N 5/0735* | (2010.01) | |
| *C12N 5/0793* | (2010.01) | |
| *C12N 5/0775* | (2010.01) | |
| *C12N 5/071* | (2010.01) | |
| *C12N 5/0797* | (2010.01) | |
| *C12N 15/90* | (2006.01) | |

(52) U.S. Cl.
CPC ............ *C12N 5/0696* (2013.01); *C12N 5/0606* (2013.01); *C12N 5/0619* (2013.01); *C12N 5/0623* (2013.01); *C12N 5/0662* (2013.01); *C12N 5/0678* (2013.01); *C12N 15/79* (2013.01); *C12N 15/907* (2013.01); *C12N 2501/603* (2013.01); *C12N 2501/605* (2013.01); *C12N 2502/13* (2013.01); *C12N 2506/08* (2013.01); *C12N 2510/00* (2013.01); *C12N 2800/00* (2013.01); *C12N 2800/108* (2013.01)

(58) Field of Classification Search
CPC ............ C12N 5/0696; C12N 2510/00; C12N 2501/603; C12N 2501/602; C12N 2501/604; C12N 2501/606; C12N 2506/1307; C12N 2501/60; C12N 2501/605; C12N 2501/608; C12N 2506/45; C12N 2506/08; C12N 5/0618; C12N 15/85; C12N 2799/027; C12N 2800/24; C12N 2800/108; C12N 15/63; C12N 2506/00; C12N 2500/99; C12N 2501/125; C12N 5/0018; C12N 5/0606; C12N 2500/90; C12N 5/0619; C12N 5/0623; C12N 5/0662; C12N 5/0678; C12N 15/79; C12N 15/907; C12N 2800/00

See application file for complete search history.

(56) References Cited

U.S. PATENT DOCUMENTS

2003/0211603 A1 * 11/2003 Earp et al. ............... 435/366
2007/0196918 A1   8/2007 Sayre et al.

FOREIGN PATENT DOCUMENTS

WO   WO 2009/032456 A2   3/2009

OTHER PUBLICATIONS

Yu et al. Induced Pluripotent Stem Cell Lines Derived from Human Somatic Cells. Science Express, Nov. 2007, pp. 1-3.*
Silva et al. Nanog promotes transfer of pluripotency after cell fusion. Nature, 2006, vol. 441, pp. 997-1001.*
Carpenter et al. Enrichment of Neurons and Neural Precursors from Human Embryonic Stem Cells. Experimental Neurology, 2001, vol. 172, pp. 383-397.*
Flax et al. Engraftable human neural stem cells respond to developmental cues, replace neurons, and express foreign genes. Nature Biotechnology, 1998, vol. 16, pp. 1033-1039.*
Jandial et al. Genetic Modification of Neural Stem Cells. Molecular Therapy, 2008, vol. 16, published online Feb. 5, 2008 pp. 450-457.*
Van Craenenbroeck et al. Episomal vectors for gene expression in mammalian cells. European J. Biochem., 2000, vol. 267, pp. 5665-5678.*
Van Craenenbroeck et al. Molecular integrity and usefulness of episomal expression vectors derived from BK and Epstein-Barr virus. Gene, 2000, vol. 253, pp. 292-301.*
Ellis et al. SOX2, a Persistent Marker for Multipotential Neural Stem Cells Derived from Embryonic Stem Cells, the Embryo or the Adult. Develop. Neurosci., 2004, vol. 26, pp. 148-165.*
Graham et al. SOX2 Functions to Maintain Neural Progenitor Identity. Neuron, 2003, vol. 39, pp. 749-765.*
Hung et al. Maintenance of Epstein-Barr virus (EBV) oriP-based episomes requires EBV-encoded nuclear antigen-1 chromosome-binding domains, which can be replaced by high-mobility group-I or histone H1. PNAS, 2001, vol. 98, pp. 1865-1870.*

(Continued)

*Primary Examiner* — Deborah Crouch
(74) *Attorney, Agent, or Firm* — Baker Botts L.L.P.

(57) ABSTRACT

Methods and compositions for the generation and use of footprint-free human induced pluripotent stem cells are provided.

7 Claims, 13 Drawing Sheets

(56) References Cited

OTHER PUBLICATIONS

Aoi, T. et-al., "Generation of pluripotent stem cells from adult mouse liver and stomach cells", Science 321:699-702, Aug. 1, 2008.

Breier, J.M. et al., "Development of a high-throughput screening assay for chemical effects on proliferation and viability of immortalized human neural progenitor cells," Toxicological Sciences (2008) 105(1):119-133.

Cezar, G.G. et al., "Identification of small molecules from human embryonic stem cells using metabolomics", Stem Cells and Development (2007) 16:869-882.

International Preliminary Report on Patentability and Written Opinion dated Sep. 27, 2011 for International PCT Application No. PCT/US2010/028524, 6 pages.

International Search Report dated Dec. 30, 2010 for International PCT Application No. PCT/US2010/028524, 3 pages.

Kaji, K. et al., "Virus-free induction of pluripotency and subsequent excision of reprogramming factors", Nature 458:771-775, Apr. 9, 2009.

Kameda, T. et al., "A severe de novo methylation of episomal vectors by human ES cells", Biochemical and Biophysical Research Communications (2006) 349:1269-1277.

Kim, J.B. et al., "Oct4-induced pluripotency in adult neural stem cells", Cell 136:411-419, Feb. 6, 2009.

Kim, J.B. et al., "Pluripotent stem cells induced from adult neural stem cells by reprogramming with two factors", Nature 454:646-650, Jul. 31, 2008.

Margolskee, R.F., "Epstein-barr based expression vectors", Current Topics in Microbiology and Immunology (1992) 158:67-95.

Muotri, A.R. et al., "Development of functional human embryonic stem cell-derived neurons in mouse brain", PNAS 102(51):18644-18648, Dec. 20, 2005.

Okita; K. et al., "Generation of germline-competent induced pluripotent stem cells", Nature 448:313-317, Jul. 19, 2007.

Okita, K. et al., "Generation of mouse induced pluripotent stem cells without viral vectors", Science 322:949-953, Nov. 7, 2008.

Park, I. et al., "Generation of human-induced pluripotent stem cells", Nature Protocols (2008) 3(7):1180-1186.

Stadtfeld, M. et al., "Defining molecular cornerstones during fibroblast to ips cell reprogramming in mouse", Cell Stem Cell 2:230-240, Mar. 2008.

Stadtfeld, M. et al., "Induced pluripotent stem cells generated without viral integration", Science 322:945-948, Nov. 7, 2008.

Takahashi, K. et al., "Induction of pluripotent stem cells from mouse embryonic and adult fibroblast cultures by defined factors", Cell 126:663-676, Aug. 25, 2006.

Yu, J. et al., "Induced pluripotent stem cell lines derived from human somatic cells", Science 318:1917-1920, Dec. 21, 2007.

Zwaka, T.P. et al., "Homologus recombination in human embryonic stem cells", Nature Biotechnology 21:319-321, Mar. 2003.

* cited by examiner

Figure 3a.
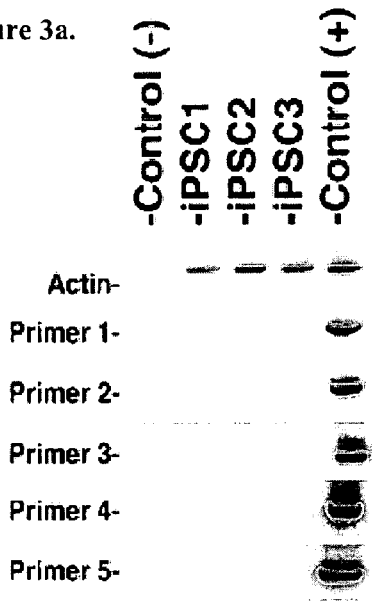
Figure 3b.
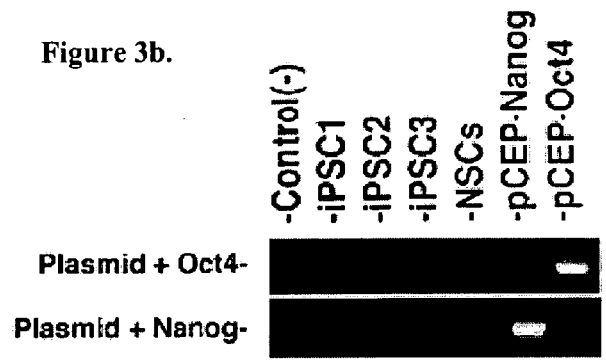
Figure 3c.
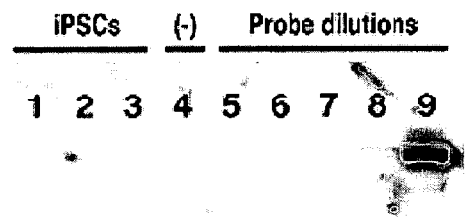
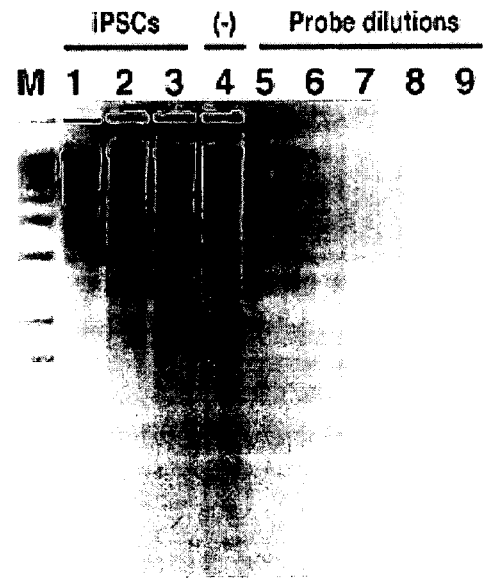

NSCs + pCEP-Oct4 and Nanog

Figure 9

Original NSC (ReNCell VM)

| Amelogenin | X | Y | D18S51 | 10 | 17 |
|---|---|---|---|---|---|
| vWA | 14 | 17 | Penta E | 7 | 21 |
| D8S1179 | 13 | 16 | D5S818 | 10 | 11 |
| TPOX | 8 | 11 | D13S317 | 10 | |
| FGA | 20 | 25 | D7S820 | 10 | |
| D3S1358 | 15 | 16 | D16S539 | 10 | 11 |
| THO1 | 6 | 9.3 | CSF1PO | 11 | 12 |
| D21S11 | 28 | 32 | Penta D | 9 | 13 | iPS colony 19 (Lenti-Oct4 + Lenti-Nanog)

| Amelogenin | X | Y | D10051 | 10 | 17 |
|---|---|---|---|---|---|
| vWA | 14 | 17 | Penta E | 7 | 21 |
| D8S1179 | 13 | 16 | D5S818 | 10 | 11 |
| TPOX | 8 | 11 | D13S317 | 10 | |
| FGA | 20 | 25 | D7S820 | 10 | |
| D3S1358 | 15 | 16 | D16S539 | 10 | 11 |
| THO1 | 6 | 9.3 | CSF1PO | 11 | 12 |
| D21S11 | 28 | 32 | Penta D | 9 | 13 | iPS colony 1 (pCEP-Oct4 + pCEP-Nanog)

| Amelogenin | X | Y | D18S51 | 10 | 17 |
|---|---|---|---|---|---|
| vWA | 14 | 17 | Penta E | 7 | 21 |
| D8S1179 | 13 | 16 | D5S818 | 10 | 11 |
| TPOX | 8 | 11 | D13S317 | 10 | |
| FGA | 20 | 25 | D7S820 | 10 | |
| D3S1358 | 15 | | 16S539 | 10 | 11 |
| THO1 | 6 | | SF1PO | 11 | 12 |
| D21S11 | 28 | 32 | Penta D | 9 | 13 |

Figure 11

NM_178033|, CYP4X1, cytochrome P450, family 4, subfamily X
NM_003930|, SCAP2, src family associated phosphoprotein 2
NM_130386|, COLEC12, collectin sub-family member 12 isoform 1
NM_000090|, COL3A1, alpha 1 type III collagen
NM_000393|, COL5A2, alpha 1 type V collagen preproprotein
NM_003070|, SMARCA2, SWI/SNF-related matrix associated
NM_013231|, FLRT1, fibronectin leucine rich transmembrane protein
NM_000104|, CYP1B1, cytochrome P450, family 1, subfamily B
NM_007361|, NID2, nidogen 2
NM_001555|, IGSF1, immunoglobulin superfamily, member 1 isoform 1
NM_006988|, ADAMTS1, a disintegrin and metalloprotease with
NM_003701|, TNFSF11, tumor necrosis factor ligand superfamily, member
NM_001010000|, ARHGAP28, Rho GTPase activating protein 28 isoform a
NM_153362|, PRSS35, protease, serine, 35
NM_021110|, COL14A1, collagen, type XIV, alpha 1
NM_024615|, PARP8, poly {ADP-ribose} polymerase family, member 8
NM_031302|, GLT8D2, glycosyltransferase 8 domain containing 2
NM_013243|, SCG3, secretogranin III
NM_003155|, STC1, stanniocalcin 1
NM_133477|, SYMPO2, synaptopodin 2
NM_003155|, STC1, stanniocalcin 1
NM_002522|, NPTX1, neuronal pentraxin I precursor
NM_003385|, VSNL1, visinin-like 1
NM_003385|, VSNL1, visinin-like 1
NM_012449|, STEAP, six transmembrane epithelial antigen of the
NM_003182|, TAC1, tachykinin 1 isoform beta precursor
NM_032551|, GPR54, G protein-coupled receptor 54
NM_052966|, C1orf24, niban protein
NM_007191|, WIFI, Wnt inhibitory factor-1 precursor
NM_005059|, RLN2, relaxin 2 isoform 2
NM_016206|, VGL-3, colon carcinoma related protein
NM_020958|, KIAA1622, HEAT-like repeat-containing protein isoform 2
NM_013244|, HGNT-IV-H, UDP-N-acetylglucosamine:a-1,3-D-mannoside
NM_003068|, SNAI2, snail 2
NM_002123|, HLA-DQB1, major histocompatibility complex, class II, DQ
NM_018018|, SLC38A4, solute carrier family 38, member 4
NM_003617|, HGS5, regulator of G-protein signalling 5
NM_004369|, COL6A4, alpha 3 type VI collagen isoform 1 precursor
NM_007197|, FZD10, frizzled 10
NM_012242|, DKK1, dickkopf homolog 1
NM_003839|, TNFRSF11A, tumor necrosis factor receptor superfamily,
NM_002994|, CXCL5, chemokine {C-X-C motif} ligand 5 precursor
NM_138786|, LOC116441, hypothetical protein BC014339
NM_002993|, CXCL6, chemokine {C-X-C motif} ligand 6 (granulocyte
NM_030923|, DKFZP566N034, hypothetical protein KDFZp566N034
NM_002994|, CXCL5, chemokine {C-X-C motif} ligand 5 precursor
NM_006183|, NTS, neurotensin/neuromedin N preproprotein
NM_005257|, GATA6, GATA binding protein 6
NM_020805|, KLHL14, kelch-like 14
NM_005794|, DHRF2, dehydrogenase/reductase (SDR family) member 2
NM_003706|, PLA2G4C, phospholipase A2, grouop IVC
NM_001884|, HAPLN1, cartilage linking protein 1
NM_002345|, LUM, lumican
NM_022068|, FAM38B, family with sequence similarity 38, member B
NM_001717|, BNC1, basonuclin 1
NM_003007|, SEMg1, semenogelin I isoform a preproprotein
NM_005161|, AGTRL1, angiotensin II receptor-like 1
NM_003176|, SYCP1, synaptonemal complex protein 1
NM_000090|, COL3A1, alpha 1 type III collagen
NM_019117|, KLHL4, kelch-like 4 isoform 1
NM_138786|, LOC116441, hypothetical protein BC014339
NM_005181|, CA3, carbonic anhydrase III
NM_000090|, COL3A1, alpha 1 type III collagen
NM_031935|, FIBL-6, hemicentin
NM_173808|, NEGR1, neuronal growth regulator 1
NM_006658|, C7orf16, G-substrate

SEQUENCE LISTING

```
<160> NUMBER OF SEQ ID NOS: 25

<210> SEQ ID NO 1
<211> LENGTH: 24
<212> TYPE: DNA
<213> ORGANISM: Artificial Sequence
<220> FEATURE:
<223> OTHER INFORMATION: Synthetic DNA primer

<400> SEQUENCE: 1
tatgatgaca caaaccccgc ccag                                          24

<210> SEQ ID NO 2
<211> LENGTH: 24
<212> TYPE: DNA
<213> ORGANISM: Artificial Sequence
<220> FEATURE:
<223> OTHER INFORMATION: Synthetic DNA primer

<400> SEQUENCE: 2
aaagcacgag attcttcgcc ctcc                                          24

<210> SEQ ID NO 3
<211> LENGTH: 21
<212> TYPE: DNA
<213> ORGANISM: Artificial Sequence
<220> FEATURE:
<223> OTHER INFORMATION: Synthetic DNA primer

<400> SEQUENCE: 3
gaaaaagcct gaactcaccg c                                             21

<210> SEQ ID NO 4
<211> LENGTH: 24
<212> TYPE: DNA
<213> ORGANISM: Artificial Sequence
<220> FEATURE:
<223> OTHER INFORMATION: Synthetic DNA primer

<400> SEQUENCE: 4
aaagcacgag attcttcgcc ctcc                                          24
```

```
<210> SEQ ID NO 5
<211> LENGTH: 21
<212> TYPE: DNA
<213> ORGANISM: Artificial Sequence
<220> FEATURE:
<223> OTHER INFORMATION: Synthetic DNA primer

<400> SEQUENCE: 5
ggcgaagaat ctcgtgcttt c                                              21

<210> SEQ ID NO 6
<211> LENGTH: 22
<212> TYPE: DNA
<213> ORGANISM: Artificial Sequence
<220> FEATURE:
<223> OTHER INFORMATION: Synthetic DNA primer

<400> SEQUENCE: 6
cggtgtcgtc catcacagtt tg                                             22

<210> SEQ ID NO 7
<211> LENGTH: 25
<212> TYPE: DNA
<213> ORGANISM: Artificial Sequence
<220> FEATURE:
<223> OTHER INFORMATION: Synthetic DNA primer

<400> SEQUENCE: 7
cgcaaggaat cggtcaatac actac                                          25

<210> SEQ ID NO 8
<211> LENGTH: 20
<212> TYPE: DNA
<213> ORGANISM: Artificial Sequence
<220> FEATURE:
<223> OTHER INFORMATION: Synthetic DNA primer

<400> SEQUENCE: 8
tccatacaag ccaaccacgg                                                20

<210> SEQ ID NO 9
<211> LENGTH: 22
<212> TYPE: DNA
<213> ORGANISM: Artificial Sequence
<220> FEATURE:
<223> OTHER INFORMATION: Synthetic DNA primer

<400> SEQUENCE: 9
ggatttcggc tccaacaatg tc                                             22

<210> SEQ ID NO 10
<211> LENGTH: 21
<212> TYPE: DNA
<213> ORGANISM: Artificial Sequence
<220> FEATURE:
<223> OTHER INFORMATION: Synthetic DNA primer

<400> SEQUENCE: 10
tgaacaaacg acccaacacc c                                              21

<210> SEQ ID NO 11
<211> LENGTH: 21
<212> TYPE: DNA
<213> ORGANISM: Artificial Sequence
<220> FEATURE:
<223> OTHER INFORMATION: Synthetic DNA primer
```

<400> SEQUENCE: 11
gcgtggatag cggtttgact c                                          21

<210> SEQ ID NO 12
<211> LENGTH: 19
<212> TYPE: DNA
<213> ORGANISM: Artificial Sequence
<220> FEATURE:
<223> OTHER INFORMATION: Synthetic DNA primer

<400> SEQUENCE: 12
aaatccgaag ccaggtgtc                                             19

<210> SEQ ID NO 13
<211> LENGTH: 18
<212> TYPE: DNA
<213> ORGANISM: Artificial Sequence
<220> FEATURE:
<223> OTHER INFORMATION: Synthetic DNA primer

<400> SEQUENCE: 13
cagtcggatg cttcaaag                                              18

<210> SEQ ID NO 14
<211> LENGTH: 20
<212> TYPE: DNA
<213> ORGANISM: Artificial Sequence
<220> FEATURE:
<223> OTHER INFORMATION: Synthetic DNA primer

<400> SEQUENCE: 14
cctatgcctg tgatttgtgg                                            20

<210> SEQ ID NO 15
<211> LENGTH: 20
<212> TYPE: DNA
<213> ORGANISM: Artificial Sequence
<220> FEATURE:
<223> OTHER INFORMATION: Synthetic DNA primer

<400> SEQUENCE: 15
ctgggacctt gtcttccttt                                            20

<210> SEQ ID NO 16
<211> LENGTH: 26
<212> TYPE: DNA
<213> ORGANISM: Artificial Sequence
<220> FEATURE:
<223> OTHER INFORMATION: Synthetic DNA primer

<400> SEQUENCE: 16
gccctctccc tccctccac gcacag                                      26

<210> SEQ ID NO 17
<211> LENGTH: 26
<212> TYPE: DNA
<213> ORGANISM: Artificial Sequence
<220> FEATURE:
<223> OTHER INFORMATION: Synthetic DNA primer

<400> SEQUENCE: 17
cggcgccgtt gctcacagac cacagg                                     26

```
<210> SEQ ID NO 18
<211> LENGTH: 20
<212> TYPE: DNA
<213> ORGANISM: Artificial Sequence
<220> FEATURE:
<223> OTHER INFORMATION: Synthetic DNA primer

<400> SEQUENCE: 18
tctgtggaga acgacatcca                                                     20

<210> SEQ ID NO 19
<211> LENGTH: 21
<212> TYPE: DNA
<213> ORGANISM: Artificial Sequence
<220> FEATURE:
<223> OTHER INFORMATION: Synthetic DNA primer

<400> SEQUENCE: 19
ctgtacgtct cagctctgtg a                                                   21

<210> SEQ ID NO 20
<211> LENGTH: 19
<212> TYPE: DNA
<213> ORGANISM: Artificial Sequence
<220> FEATURE:
<223> OTHER INFORMATION: Synthetic DNA primer

<400> SEQUENCE: 20
aaaagcccac tccagcatc                                                      19

<210> SEQ ID NO 21
<211> LENGTH: 20
<212> TYPE: DNA
<213> ORGANISM: Artificial Sequence
<220> FEATURE:
<223> OTHER INFORMATION: Synthetic DNA primer

<400> SEQUENCE: 21
cagacaatcc agcacatctc                                                     20

<210> SEQ ID NO 22
<211> LENGTH: 20
<212> TYPE: DNA
<213> ORGANISM: Artificial Sequence
<220> FEATURE:
<223> OTHER INFORMATION: Synthetic DNA primer

<400> SEQUENCE: 22
ctccttcagg cagtgagagc                                                     20

<210> SEQ ID NO 23
<211> LENGTH: 20
<212> TYPE: DNA
<213> ORGANISM: Artificial Sequence
<220> FEATURE:
<223> OTHER INFORMATION: Synthetic DNA primer

<400> SEQUENCE: 23
gagatgcagt gtgctcgtgc                                                     20

<210> SEQ ID NO 24
<211> LENGTH: 20
<212> TYPE: DNA
<213> ORGANISM: Artificial Sequence
<220> FEATURE:
<223> OTHER INFORMATION: Synthetic DNA primer
```

```
<400> SEQUENCE: 24
accacagtcc atgccatcac                                               20

<210> SEQ ID NO 25
<211> LENGTH: 20
<212> TYPE: DNA
<213> ORGANISM: Artificial Sequence
<220> FEATURE:
<223> OTHER INFORMATION: Synthetic DNA primer

<400> SEQUENCE: 25
tccaccaccc tgttgctgta                                               20
```

INDUCED PLURIPOTENT STEM CELL PRODUCED BY TRANSFECTING A HUMAN NEURAL STEM CELL WITH AN EPISOMAL VECTOR ENCODING THE OCT4 AND NANOG PROTEINS

CROSS-REFERENCE TO RELATED APPLICATIONS

This application is a national phase application of PCT Application No. 2010/028524, filed Mar. 24, 2010, which claims the benefit of U.S. Provisional Application No. 61/163,379, filed Mar. 25, 2009, the contents of which are incorporated herein by reference in their entirety for all purposes.

STATEMENT AS TO RIGHTS TO INVENTIONS MADE UNDER FEDERALLY SPONSORED RESEARCH OR DEVELOPMENT

This invention was made with government support under NS-050217 awarded by the National Institutes of Health. The Government has certain rights in the invention.

BACKGROUND OF THE INVENTION

Genetic reprogramming of somatic cells to a pluripotent state (induced pluripotent stem cells or iPSCs) by over-expression of specific genes has been accomplished using mouse and human cells. The resulting iPSCs are isogenic to the donor individual, i.e., they carry a similar genetic background, and are thus attractive not only for future therapeutic purposes, with lower risk of immune rejection, but also for understanding complex diseases with heritable and sporadic conditions. However, there are several obstacles to overcome before iPSCs might be considered for cellular therapy; for example, the use of oncogenes and insertional mutagenesis by delivery viruses may induce malignant cell transformation.

Genetic reprogramming to a pluripotent state of mouse somatic differentiated cells was first achieved by ectopic expression of four factors (Oct4, Sox2, Klf4 and c-Myc) using retroviruses (Takahashi, K. & Yamanaka, S., *Cell*, 2006). Such cells were named induced pluripotent stem cells (iPSCs). Subsequently, the method was applied to human cells using the same factors or a different combination in a lentivirus vector (Oct4, Sox2, Lin28 and Nanog) (Takahashi, K. et al., *Cell*, 2007; Yu, J. et al., *Science*, 2007; Lowry, W. E. et al., *Proc Natl Acad Sci USA*, 2008; Park, I. H. et al., *Nature protocols*, 2008). Both mouse and human iPSCs seem similar to embryonic stem cells (ESCs) with respect to their morphology, cell behavior, gene expression, epigenetic status and differentiation potential in culture. However, insertional mutagenesis generated by the use of retroviruses increases the risk of tumorigenicity, precluding subsequent safe cellular transplantation (Kustikova, O. et al., *Science*, 2005). Viral vectors are also known to induce a transcriptional response from target cells, altering their behavior and sometimes inducing apoptosis (Best, S. M., *Annu Rev Microbiol*, 2008). Moreover, reactivation of viral transgene was also implicated in tumorigenesis from iPSC-derived chimeric mice (Nakagawa, M. et al., *Nat Biotechnol*, 2008). Finally, random integration may influence the molecular signatures of iPSCs by interrupting regulatory regions in the human genome. iPSCs from mouse fibroblasts were generated using multiple adenoviral infections at an extremely low efficiency (Stadtfeld, M. et al., *Science*, 2008). A problem with adenovirus mediated transfections is that adenoviral genes may integrate in the genome and induce an immune reaction in humans, raising safety concerns for future therapeutic applications. Recently, iPSCs were generated by transient expression of Oct4, Sox2 and Klf4 from mouse embryonic fibroblasts (Okita, K. et al., *Science*, 2008). Also, a two-step seamless factor removal from iPS using transposase-stimulated excision was recently reported (Kaji, K. et al., Nature 2009; Woltjen, K et al., Nature 2009). However, these studies need further validation in more rigorous pluripotent assays.

The methods and compositions described herein overcome these and other problems in the art.

SUMMARY OF THE INVENTION

Provided herein are, inter alia, highly efficient methods and compositions for making and using a footprint-free human induced pluripotent stem cell. The footprint-free human induced pluripotent stem cell may be generated by transfection of a neural stem cell without the use of a viral transfection system.

In one aspect, a method for preparing a footprint-free human induced pluripotent stem cell is provided. The method includes transfecting a human neural stem cell with a nucleic acid encoding an Oct4 protein. The transfection of the neural stem cell is performed without the use of a viral transfection system. The transfected neural stem cell is allowed to divide and thereby forms the footprint-free human induced pluripotent stem cell. In some embodiments, prior to allowing the transfected neural stem cell to divide, the method also includes transfecting the human neural stem cell with a nucleic acid encoding a Nanog protein.

In another aspect, a footprint-free human induced pluripotent stem cell is provided.

In another aspect, a footprint-free human induced pluripotent stem cell is prepared according to methods provided herein.

In another aspect, a human neural stem cell is provided. The human neural stem cell includes a nucleic acid encoding an Oct4 protein forming part of a plasmid and a nucleic acid encoding a Nanog protein forming part of a plasmid.

In another aspect, a method for producing a human somatic cell is provided. The method includes contacting a footprint-free human induced pluripotent stem cell with cellular growth factors and allowing the footprint-free human induced pluripotent stem cell to divide, thereby forming the human somatic cell.

In another aspect, a method of treating a mammal in need of tissue repair is provided. The method includes administering a footprint-free human induced pluripotent stem cell to the mammal and allowing the footprint-free human induced pluripotent stem cell to divide and differentiate into somatic cells in the mammal, thereby providing tissue repair in the mammal.

BRIEF DESCRIPTION OF THE DRAWINGS

(FIG. 1a) Morphology of human fetal NSCs before lentiviral infection. Inset: after 3 days post-infection with Lenti-Oct4 and Lenti-Nanog, individual cells express alkaline phosphatase (AP). (FIG. 1b) Example of infected plates stained for AP at 14 days post-infection showing several AP-positive colonies. Control (either Lenti-Oct4 or Lenti-Nanog alone) did not result in any AP-positive colony. (FIG. 1c) and (FIG. 1d) Aspect of colonies 14 days after infection growing in MEFs. (FIG. 1e)

Established human iPSC colonies, with well-defined border and compact cells, are morphologically similar to hESCs. (FIG. 1f) Typical image of iPSCs growing in feeder-free conditions. (FIG. 1g) Representative immunofluorescence analysis of iPSCs growing on matrigel. Clear expression of pluripotent markers is observed. Bar=150 µm.

(FIG. 2a) Aspect of human NSCs after plasmid electroporation and plating on MEFs. (FIG. 2b) and (FIG. 2c) Some selected colonies display a strong differentiation tendency in feeder-free conditions. (FIG. 2d) Established iPSC lines are morphologically similar to hESCs. (FIG. 2e) and (FIG. 2f) iPSCs have a large nucleus-to-cytoplasm ratio and prominent nucleoli when compared to original NSCs. (FIG. 2g) Immunofluorescence analysis of iPSCs growing on matrigel showed clear expression of typical ESC markers. (FIG. 2h) In vitro differentiation of iPSCs into EBs.

FIG. 3: Absence of plasmid integration in integration-free iPSCs. (FIG. 3a) and (FIG. 3b) PCR analyses for plasmid integration in genomic DNA from the indicated iPSC clones. (FIG. 3c) Southern blot (left) membrane hybridization of 10 µg of BamHI-digested genomic DNA (right) using a DNA probe from the pCEP backbone. Plasmid DNA of pCEP-Oct4 and PCEP-Nanog, diluted to the equivalent of 0.5 integration per genome, were used as controls. Lanes: M, DNA molecular marker; 1-iPSC1; 2-iPSC2; 3-iPSC3; 4-NSCs (negative control); 5-probe 25 ρg; 6-probe 50 ρg; 7-100 ρg; 8-200 ρg and 9-50 ρg. Arrow indicates expected probe size.

FIG. 4: Transcriptional analysis of human integration-free iPSC colonies.

FIG. 5: The dynamics of integration-free reprogramming.

FIG. 8: Sustained expression using episomal vectors.

FIG. 9: Integration-free iPSC colonies are genetically identical to the original human fetal NSCs. DNA fingerprinting analysis at 16 independent loci indicates that both iPSCs generated by lentivirus infection (iPSC colony 19) and by transient transfection with episomal vectors (iPSC colony 1) and the original human fetal NSCs (ReNCell® VM) share all alleles investigated and are different from commonly available hESC lines.

(FIGS. 10c-d): Staining with human-specific nestin and DCX antibody show well organized nestin positive cells in primitive neuronal tube and numerous postmitotic DCX-positive neurons at the periphery.

FIG. 11: Refseq-annotated genes that were upregulated in iPSCs relative to both hESCs and NSC. Panel illustrates marker genes implicated in pluripotency of NSCs.

FIG. 12 depicts an assessment of the change in myc levels from selected iPSCs derived from NSCs after reprogramming. Histogram legend: ordinate (myc levels in arbitrary units); abscissa (iPSC1, iPSC2, Cyt25, HUES6 and NSC).

DETAILED DESCRIPTION OF THE INVENTION

I. Definitions

Figure 1:
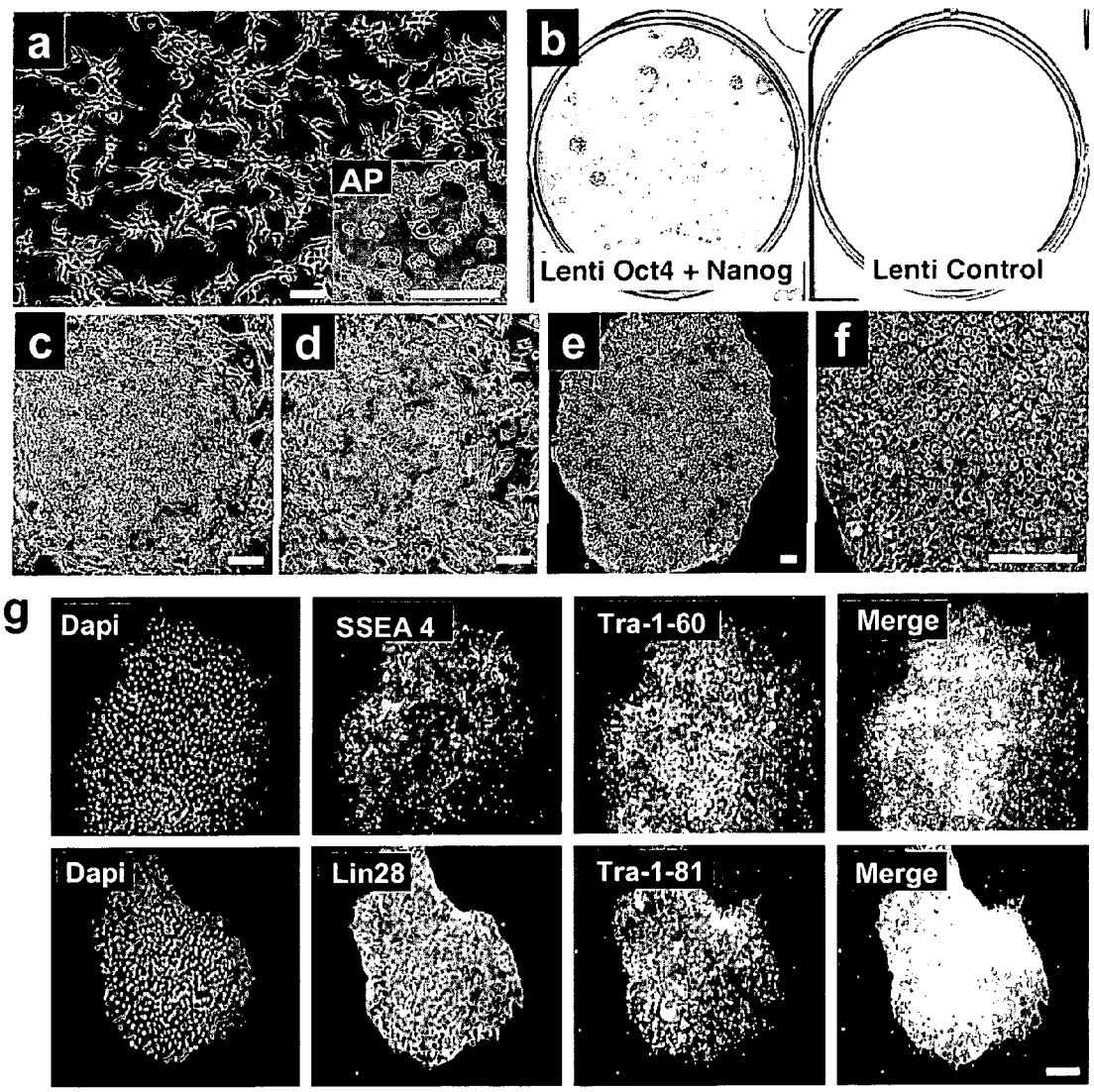
FIG. 1: Efficient and rapid generation of iPSCs from human fetal NSCs using two factors.

The following definitions are provided to facilitate understanding of certain terms used frequently herein and are not meant to limit the scope of the present disclosure.

"Nucleic acid" refers to deoxyribonucleotides or ribonucleotides and polymers thereof in either single- or double-stranded form, and complements thereof.

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

The terms "identical" or percent "identity," in the context of two or more nucleic acids, refer to two or more sequences or subsequences that are the same or have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. See, e.g., NCBI web site at ncbi.nlm.nih.gov/BLAST/ or the like. Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

The phrase "stringent hybridization conditions" refers to conditions under which a probe will hybridize to its target sequence, typically in a complex mixture of nucleic acids, but to not other sequences. Stringent conditions are sequence-dependent and will be different in different circumstances. Longer sequences hybridize specifically at higher temperatures. An extensive guide to the hybridization of nucleic acids is found in Tijssen, TECHNIQUES IN BIOCHEMISTRY AND MOLECULAR BIOLOGY—HYBRIDIZATION WITH NUCLEIC PROBES, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

A variety of methods of specific DNA and RNA measurement that use nucleic acid hybridization techniques are known to those of skill in the art (see, Sambrook, supra). Some methods involve electrophoretic separation (e.g., Southern blot for detecting DNA, and Northern blot for detecting RNA), but measurement of DNA and RNA can also be carried out in the absence of electrophoretic separation (e.g., by dot blot).

The sensitivity of the hybridization assays may be enhanced through use of a nucleic acid amplification system that multiplies the target nucleic acid being detected. Examples of such systems include the polymerase chain reaction (PCR) system and the ligase chain reaction (LCR) system. Other methods recently described in the art are the nucleic acid sequence based amplification (NASBA, Cangene, Mississauga, Ontario) and Q Beta Replicase systems. These systems can be used to directly identify mutants where the PCR or LCR primers are designed to be extended or ligated only when a selected sequence is present. Alternatively, the selected sequences can be generally amplified using, for example, nonspecific PCR primers and the amplified target region later probed for a specific sequence indicative of a mutation. It is understood that various detection probes, including Taqman and molecular beacon probes can be used to monitor amplification reaction products, e.g., in real time.

The word "polynucleotide" refers to a linear sequence of nucleotides. The nucleotides can be ribonucleotides, deoxyribonucleotides, or a mixture of both. Examples of polynucleotides contemplated herein include single and double stranded DNA, single and double stranded RNA (including miRNA), and hybrid molecules having mixtures of single and double stranded DNA and RNA.

The words "protein", "peptide", and "polypeptide" are used interchangeably to denote an amino acid polymer or a set of two or more interacting or bound amino acid polymers.

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The terms "transfection" or "transfected" are defined by a process of introducing nucleic acid molecules into a cell by non-viral methods. The nucleic acid molecules may be gene sequences encoding complete proteins or functional portions thereof.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell (Sambrook et al., 1989 *Molecular Cloning: A Laboratory Manual*, 18.1-18.88).

Expression of a transfected gene can occur transiently or stably in a cell. During "transient expression" the transfected gene is not transferred to the daughter cell during cell division. Since its expression is restricted to the transfected cell, expression of the gene is lost over time. In contrast, stable expression of a transfected gene can occur when the gene is co-transfected with another gene that confers a selection advantage to the transfected cell. Such a selection advantage may be a resistance towards a certain toxin that is presented to the cell.

The term "plasmid" refers to a nucleic acid molecule that encodes for genes and/or regulatory elements necessary for the expression of genes. Expression of a gene from a plasmid can occur in cis or in trans. If a gene is expressed in cis, gene and regulatory elements are encoded by the same plasmid. Expression in trans refers to the instance where the gene and the regulatory elements are encoded by separate plasmids.

The term "episomal" refers to the extra-chromosomal state of a plasmid in a cell. Episomal plasmids are nucleic acid molecules that are not part of the chromosomal DNA and replicate independently thereof.

A "cell culture" is a population of cells residing outside of an organism. These cells are optionally primary cells isolated from a cell bank, animal, or blood bank, or secondary cells that are derived from one of these sources and have been immortalized for long-lived in vitro cultures.

A "stem cell" is a cell characterized by the ability of self-renewal through mitotic cell division and the potential to differentiate into a tissue or an organ. Among mammalian stem cells, embryonic and somatic stem cells may be distinguished. Embryonic stem cells may reside in the blastocyst and give rise to embryonic tissues, whereas somatic stem cells may reside in adult tissues for the purpose of tissue regeneration and repair.

The term "pluripotent" or "pluripotency" refers to cells with the ability to give rise to progeny that can undergo differentiation, under appropriate conditions, into cell types that collectively exhibit characteristics associated with cell lineages from the three germ layers (endoderm, mesoderm, and ectoderm). Pluripotent stem cells can contribute to tissues of a prenatal, postnatal or adult organism. A standard art-accepted test, such as the ability to form a teratoma in 8-12 week old SCID mice, can be used to establish the pluripotency of a cell population. However, identification of various pluripotent stem cell characteristics can also be used to identify pluripotent cells.

"Pluripotent stem cell characteristics" refer to characteristics of a cell that distinguish pluripotent stem cells from other cells. Expression or non-expression of certain combinations of molecular markers are examples of characteristics of pluripotent stem cells. More specifically, human pluripotent stem cells may express at least some, and optionally all, of the markers from the following non-limiting list: SSEA-3, SSEA-4, TRA-1-60, TRA-1-81, TRA-2-49/6E, ALP, Sox2, E-cadherin, UTF-1, Oct4, Lin28, Rex1, and Nanog. Cell morphologies associated with pluripotent stem cells are also pluripotent stem cell characteristics.

The term "reprogramming" refers to the process of dedifferentiating a non-pluripotent cell into a cell exhibiting pluripotent stem cell characteristics.

The term "treating" means ameliorating, suppressing, eradicating, and/or delaying the onset of the disease being treated.

II. Methods of Preparing Footprint-Free Human Induced Pluripotent Stem Cells

In one aspect, a method for preparing a footprint-free human induced pluripotent stem cell is provided. The method includes transfecting a human neural stem cell with a nucleic acid encoding an Oct4 protein to form a transfected human neural stem cell. The transfection of the neural stem cell is performed without the use of a viral transfection system. The transfected neural stem cell is allowed to divide and thereby forms the footprint-free human induced pluripotent stem cell. In some embodiments, prior to allowing the transfected neural stem cell to divide, the method also includes transfecting the human neural stem cell with a nucleic acid encoding a Nanog protein. Thus, in some embodiments, the method includes transfecting a human neural stem cell with a nucleic acid encoding an Oct4 protein and a nucleic acid encoding a Nanog protein to form a transfected human neural stem cell followed by allowing the transfected neural stem cell to divide thereby forming the footprint-free human induced pluripotent stem cell.

A "human induced pluripotent stem cell" refers to a human pluripotent stem cell artificially derived from a human non-pluripotent cell. A non-pluripotent cell can be a cell of lesser potency to self-renew and differentiate than a pluripotent stem cell. Cells of lesser potency can be, but are not limited to, somatic stem cells, tissue specific progenitor cells, primary or secondary cells. Without limitation, a somatic stem cell can be a hematopoietic stem cell, a mesenchymal stem cell, an epithelial stem cell, a skin stem cell or a neural stem cell. A tissue specific progenitor refers to a cell devoid of self-renewal potential that is committed to differentiate into a specific organ or tissue. A primary cell includes any cell of an adult or fetal organism apart from egg cells, sperm cells and stem cells. Examples of useful primary cells include, but are not limited to, skin cells, bone cells, blood cells, cells of internal organs and cells of connective tissue. A secondary cell is derived from a primary cell and has been immortalized for long-lived in vitro cell culture.

A "footprint-free human induced pluripotent stem cell" refers to a human induced pluripotent stem cell that is devoid of any detectable genomic integration event following transfection of the non-pluripotent cell. The genome of a footprint-free human induced pluripotent stem cell does not contain any detectable parts of the nucleic acid molecules initially transfected into the non-pluripotent cell. In some embodiments, "detectable genomic integration event" refers to detectable integration of transfected nucleic acid molecules, or portions thereof, into the genome of a human induced pluripotent stem cell. Any appropriate method of detecting integration may be employed, such as polymerase chain reaction and Southern Blot hybridization. In some embodiments, Southern Blot hybridization is used to detect integration. Where Southern Blot hybridization is used to detect integration, a "footprint-free human induced pluripotent stem cell" refers to a human induced pluripotent stem cell that is devoid of a genomic integration event as detected by Southern Blot hybridization. In some embodiments, a "footprint-free human induced pluripotent stem cell" refers to a human induced pluripotent stem cell devoid of any genomic integration.

The term "transfection" or "transfecting" is defined as a process of introducing nucleic acid molecules into a cell by non-viral methods. Any appropriate transfection method that does not use viral DNA or viral particles as a delivery system to introduce the nucleic acid molecule into the cell is useful in the methods described herein. Exemplary transfection methods include calcium phosphate transfection, liposomal transfection, nucleofection, sonoporation, transfection through heat shock, magnetifection and electroporation. In some embodiments, the nucleic acid molecules are introduced into a cell using electroporation following standard procedures well known in the art.

An "Oct4 protein" as referred to herein includes any of the naturally-occurring forms of the Octomer 4 transcription factor, or variants thereof that maintain Oct4 transcription factor activity (e.g. within at least 50%, 80%, 90% or 100% activity compared to Oct4). In some embodiments, variants have at least 90% amino acid sequence identity across their whole sequence compared to the naturally occurring Oct4 polypeptide. In other embodiments, the Oct4 protein is the protein as identified by the NCBI reference gi:42560248 and gi:116235491 corresponding to isoform 1 and 2.

A "Nanog protein" as referred to herein includes any of the naturally-occurring forms of the Nanog transcription factor, or variants thereof that maintain Nanog transcription factor activity (e.g. within at least 50%, 80%, 90% or 100% activity compared to Nanog). In some embodiments, variants have at least 90% amino acid sequence identity across their whole sequence compared to the naturally occurring Nanog polypeptide. In other embodiments, the Nanog protein is the protein as identified by the NCBI reference gi:153945816.

In some embodiments, the method provided herein do not include the use of viral transfection systems. Viral transfection systems employ viral nucleic acid and protein to transfect a nucleic acid molecule into a cell. In the presence of viral nucleic acid and protein, the transfected nucleic acid molecule is able to integrate into the cellular genome, therefore becoming part of the genome. Such integration of the transfected nucleic acid molecules into the genome may be undesirable, since it may prevent the generation of footprint-free human induced pluripotent stem cells. Thus, viral transfection systems typically do not provide a "footprint-free human induced pluripotent stem cell".

Allowing the transfected neural stem cell to divide and thereby forming the footprint-free human induced pluripotent stem cell may include expansion of the neural stem cell after transfection, optional selection for transfected cells and identification of pluripotent stem cells. Expansion as used herein includes the production of progeny cells by a transfected neural stem cell in containers and under conditions well know in the art. Expansion may occur in the presence of suitable media and cellular growth factors. Cellular growth factors are agents which cause cells to migrate, differentiate, transform or mature and divide. They are polypeptides which can usually be isolated from various normal and malignant mammalian cell types. Some growth factors can also be produced by genetically engineered microorganisms, such as bacteria (*E. coli*) and yeasts. Cellular growth factors may be supplemented to the media and/or may be provided through co-culture with irradiated embryonic fibroblast that secrete such cellular growth factors. Examples of cellular growth factors include, but are not limited to, FGF, bFGF2, and EGF.

Where appropriate the expanding neural stem cell may be subjected to a process of selection. A process of selection may include a selection marker introduced into a neural stem cell upon transfection. A selection marker may be a gene encoding for a polypeptide with enzymatic activity. The enzymatic activity includes, but is not limited to, the activity of an acetyltransferase and a phosphotransferase. In some embodiments, the enzymatic activity of the selection marker is the activity of a phosphotransferase. The enzymatic activity of a selection marker may confer to a transfected neural stem cell the ability to expand in the presence of a toxin. Such a toxin typically inhibits cell expansion and/or causes cell death. Examples of such toxins include, but are not limited to, hygromycin, neomycin, puromycin and gentamycin. In some embodiments, the toxin is hygromycin. Through the enzymatic activity of a selection maker a toxin may be converted to a non-toxin which no longer inhibits expansion and causes cell death of a transfected neural stem cell. Upon exposure to a toxin a cell lacking a selection marker may be eliminated and thereby precluded from expansion.

Identification of the footprint-free human induced pluripotent stem cell may include, but is not limited to the evaluation of the afore mentioned pluripotent stem cell characteristics. Such pluripotent stem cell characteristics include without further limitation, the expression or non-expression of certain combinations of molecular markers. Further, cell morphologies associated with pluripotent stem cells are also pluripotent stem cell characteristics.

In some embodiments, the nucleic acid encoding an Oct4 protein forms part of a plasmid and the nucleic acid encoding a Nanog protein forms part of a plasmid. In another embodiment, the nucleic acid encoding an Oct4 protein and the nucleic acid encoding a Nanog protein form part of the same plasmid. In one embodiment, the nucleic acid encoding an Oct4 protein forms part of a first plasmid and the nucleic acid encoding a Nanog protein forms part of a second plasmid.

In one embodiment, the method provided herein does not include transfection of a human neural stem cell with an additional nucleic acid encoding a cMyc protein, a Sox2 protein, a Lin28 protein or a KLF4 protein.

A "cMyc protein" as referred to herein includes any of the naturally-occurring forms of the cMyc transcription factor, or variants thereof that maintain cMyc transcription factor activity (e.g. within at least 50%, 80%, 90% or 100% activity compared to cMyc). In some embodiments, variants have at least 90% amino acid sequence identity across their whole sequence compared to the naturally occurring cMyc polypeptide. In other embodiments, the cMyc protein is the protein as identified by the NCBI reference gi:71774083.

A "Sox2 protein" as referred to herein includes any of the naturally-occurring forms of the Sox2 transcription factor, or variants thereof that maintain Sox2 transcription factor activity (e.g. within at least 50%, 80%, 90% or 100% activity compared to Sox2). In some embodiments, variants have at least 90% amino acid sequence identity across their whole sequence compared to the naturally occurring Sox2 polypeptide. In other embodiments, the Sox2 protein is the protein as identified by the NCBI reference gi:28195386.

A "Lin28 protein" as referred to herein includes any of the naturally-occurring forms of the Lin28 transcription factor, or variants thereof that maintain Lin28 transcription factor activity (e.g. within at least 50%, 80%, 90% or 100% activity compared to Lin28). In some embodiments, variants have at least 90% amino acid sequence identity across their whole sequence compared to the naturally occurring Lin28 polypeptide. In other embodiments, the Lin28 protein is the protein as identified by the NCBI reference gi:13375938.

A "KLF4 protein" as referred to herein includes any of the naturally-occurring forms of the KLF4 transcription factor, or variants thereof that maintain KLF4 transcription factor activity (e.g. within at least 50%, 80%, 90% or 100% activity compared to KLF4). In some embodiments, variants have at least 90% amino acid sequence identity across their whole sequence compared to the naturally occurring KLF4 polypeptide. In other embodiments, the KLF4 protein is the protein as identified by the NCBI reference gi:194248077.

III. A Footprint-Free Human Induced Pluripotent Stem Cell

In one aspect, a footprint-free human induced pluripotent stem cell is provided. In one embodiment, the footprint-free human induced pluripotent stem cell is derived from a neural stem cell.

In another embodiment, the footprint-free human induced pluripotent stem cell is produced according to the methods provided herein. The methods described above in the section entitled "Methods of Preparing Footprint-Free Human Induced Pluripotent Stem Cells" are equally applicable to a footprint-free human induced pluripotent stem cell as provided here.

IV. Human Neural Stem Cells

Provided herein are human neural stem cells useful as intermediates in making footprint-free human induced pluripotent stem cells.

In one aspect, a human neural stem cell is provided. The human neural stem cell includes a nucleic acid encoding an Oct4 protein forming part of a plasmid. The human neural stem cell may also include a nucleic acid encoding a Nanog protein forming part of a plasmid. Thus, in some embodiments, the human neural stem cell may includes a nucleic acid encoding an Oct4 protein forming part of a plasmid and a nucleic acid encoding a Nanog protein forming part of a plasmid. In one embodiment, the human neural stem cell includes a nucleic acid encoding an Oct4 protein and a nucleic acid encoding a Nanog protein both forming part of the same plasmid. In another embodiment, the human neural stem cell includes a nucleic acid encoding an Oct4 protein forming part of a first plasmid and the nucleic acid encoding a Nanog protein forming part of a second plasmid.

In some embodiments, the human neural stem cell is isolated from a human embryo.

In another embodiment, the human neural stem cell is derived from a human embryonic stem cell.

V. Methods for Producing Human Somatic Cells from Footprint-Free Human Induced Pluripotent Stem Cells In another aspect, methods are provided herein to produce human somatic cells from footprint-free human induced pluripotent stem cells. The method includes contacting a footprint-free human induced pluripotent stem cell with cellular growth factors and allowing the footprint-free human induced pluripotent stem cell to divide, thereby forming the human somatic cell. The footprint-free human induced pluripotent stem cell is allowed to divide in the presence of appropriate media and cellular growth factors. Examples for cellular growth factors include, but are not limited to, SCF, GMCSF, FGF, TNF, IFN, EGF, IGF and members of the interleukin family. The footprint-free human induced pluripotent stem cell is prepared in accordance with the methods provided by the present invention.

In some embodiments, the method includes transfecting a human neural stem cell with a nucleic acid encoding an Oct4 protein. The method may also include transfecting said human neural stem cell with a nucleic acid encoding a Nanog protein. Thus, in some embodiments, the method includes transfecting a human neural stem cell with a nucleic acid encoding an Oct4 protein and a nucleic acid encoding a Nanog protein to form a transfected human neural stem cell. The transfection of the neural stem cell is performed without the use of a viral transfection system. The transfected neural stem cell is allowed to divide and thereby forms the footprint-free human induced pluripotent stem cell.

In another aspect, a method of treating a mammal in need of tissue repair is provided. The method includes administering a footprint-free human induced pluripotent stem cell to the mammal and allowing the footprint-free human induced pluripotent stem cell to divide and differentiate into somatic cells in the mammal, thereby providing tissue repair in the mammal. The footprint-free human induced pluripotent stem cell is prepared in accordance with the methods provided by the present invention. In some embodiments, the method includes transfecting a human neural stem cell with a nucleic acid encoding an Oct4 protein and a nucleic acid encoding a Nanog protein to form a transfected human neural stem cell. The transfection of the neural stem cell is performed without the use of a viral transfection system. The transfected neural stem cell is allowed to divide and thereby forms the footprint-free human induced pluripotent stem cell.

EXAMPLE

The timing of reprogramming a non-pluripotent cell and the factors required seem to vary depending on the cellular context (Aasen, T. et al., *Nat. Biotechnol.* (2008); Eminli, S. et al., *Stem Cells*, 26:2467-2474 (2008); Kim, J. B. et al., *Nature*, 454:646-650 (2008); Aoi, T. et al., *Science*, 321:699-702 (2008); Hanna, J. et al., *Cell*, 133:250-264 (2008)). The susceptibility of a somatic cell to convert may depend on how similar the transcriptional profile is to ESCs. Of note, mouse neural stem cells (NSCs) were reprogrammed using only two factors (Oct4 and Klf4), due to the endogenously high expression of Sox2 and c-Myc genes (Kim, J. B. et al., *Nature*, 454:646-650 (2008); Silva, J. et al., *PLoS Biol*, 6:e253 (2008)). Fibroblasts that already carry the Oct4 transgene can be reprogrammed with fewer factors, facilitating the study of nuclear reprogramming (Stadtfeld, M. et al., *Science*, 322:945-949 (2008)). Moreover, although reprogramming can be achieved without c-Myc, iPSCs generation is more efficient when the gene is presented (Okita, K. et al., *Nature*, 448:313-317 (2007); Wernig, M. et al., *Cell stem cell*, 2:10-12 (2008)). Such observations prompted the use of human NSCs as a model to facilitate the generation of iPSCs and the study of reprogramming steps. The starting material was a multipotent, karyotypically normal human NSC c-Myc-immortalized cell line, derived from the midbrain of 10-week gestation human tissue sample, with the rationale that the high expression of c-Myc and Sox2 in these cells might prompt them to reprogram more easily than previous cell types. First, it was examined whether the combination of Oct4 and Nanog would reprogram these cells to a pluripotent state (Breier, J. M. et al., *Toxicol Sci*, 105:119-133 (2008); Donato, R. et al., *BMC neuroscience*, 8:36 (2007)).

The human NSCs have a typical undifferentiated neural stem cell morphology when expanding as monolayers on laminin-coated plates (FIG. 1a). NSCs were infected with lentivirus expressing Oct4 and Nanog (ON) and plated onto a layer of irradiated mouse embryonic fibroblasts (MEFs) in human ESCs (hESC) medium (Muotri, A. R. et al., *Proc Natl Acad Sci USA*, 102:18644-18648 (2005)). Individual cells positive for alkaline phosphatase (AP), a marker for pluripotent cells, appear as early as 4 days after infection (FIG. 1a, inset). Interestingly, the efficiency was around 1%, as measured by the number of AP-positive colonies, at 14 days post-infection. In the first week after infection, hundreds of small colonies grew rapidly and had preliminary hESC morphology (FIGS. 1c, d). Two weeks after infection, iPSC colonies with a mature morphology similar to hESCs were distinguished from the original NSC population (FIGS. 1e-f). The NSCs-iPSC(ON) colonies were then manually isolated and propagated under feeder-free growth conditions on matrigel-coated dishes. They express markers of undifferentiated ESCs, including Lin28, TRA-1-60 and SSEA-4, confirming the genetic reprogramming by the two factors (FIG. 1g). Several iPSC lineages were established from independent infections and mechanically passaged at least 20 passages.

Figure 2:
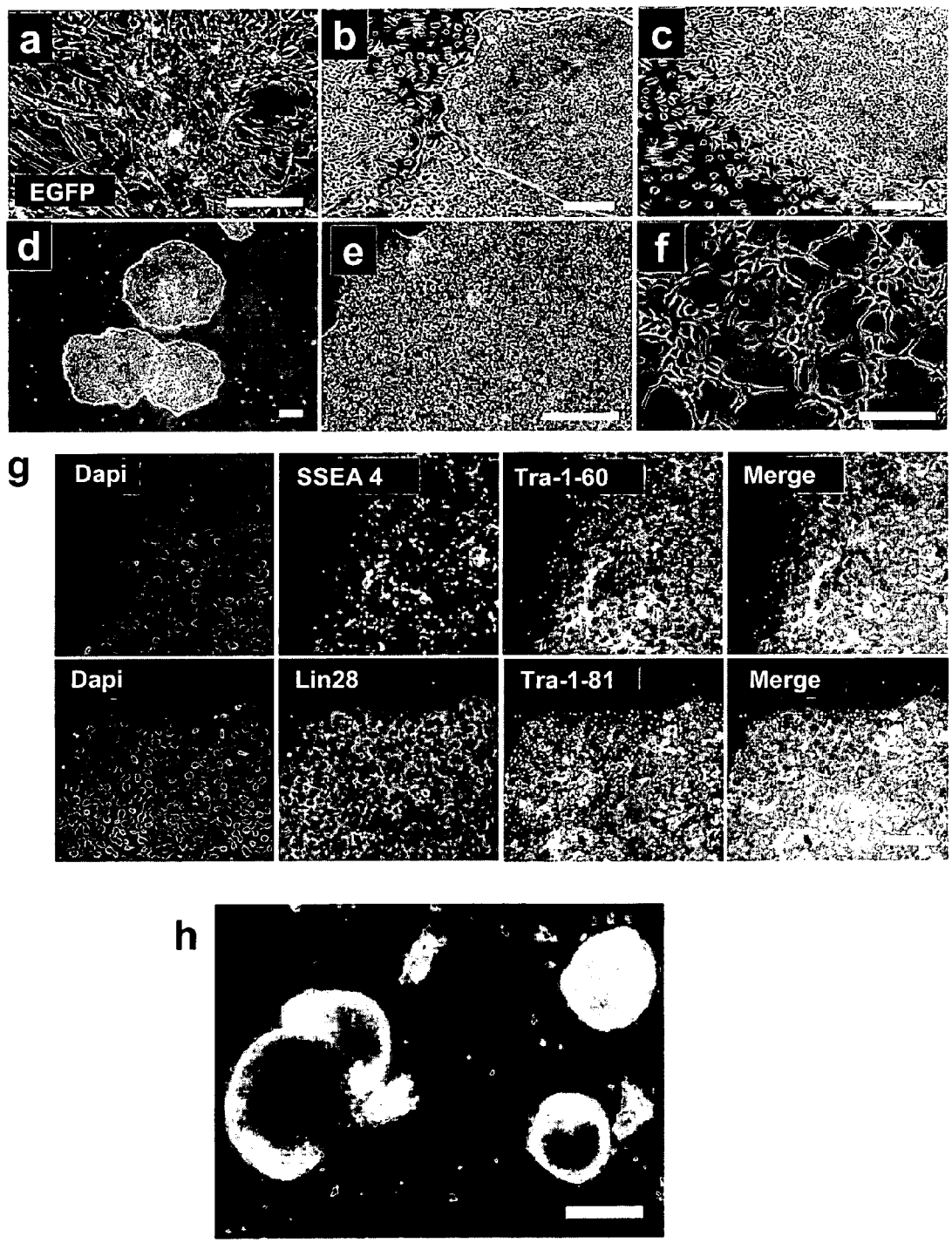
FIG. 2: Generation of integration-free human iPSCs.
Figure 2I:
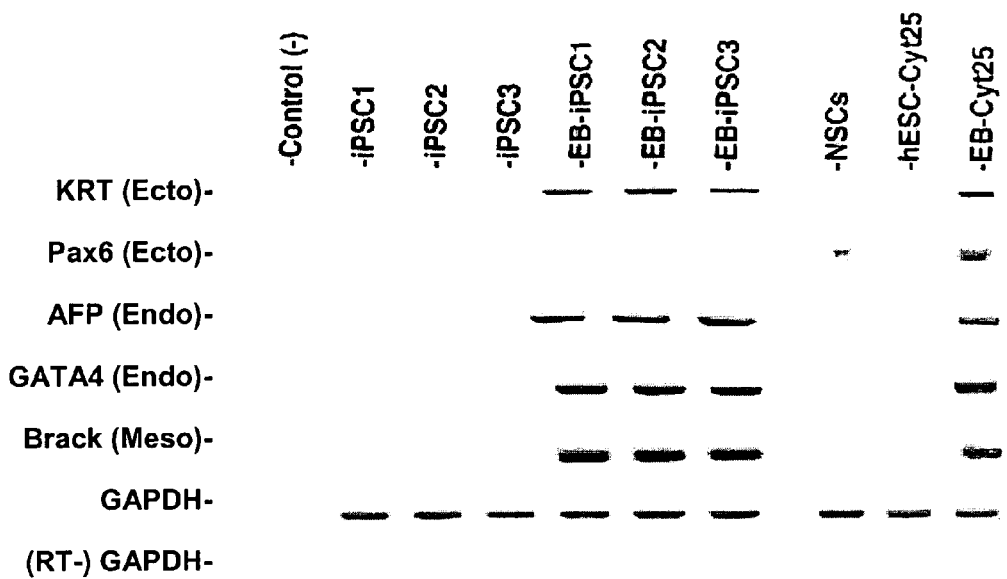
(FIG. 2i) RT-PCR from undifferentiated and EB-derived iPSCs showing expression of all three primary germ cell layers. The hESCs Cyt25 was used as a benchmark. Bar=150 µm.
Figure 2J:
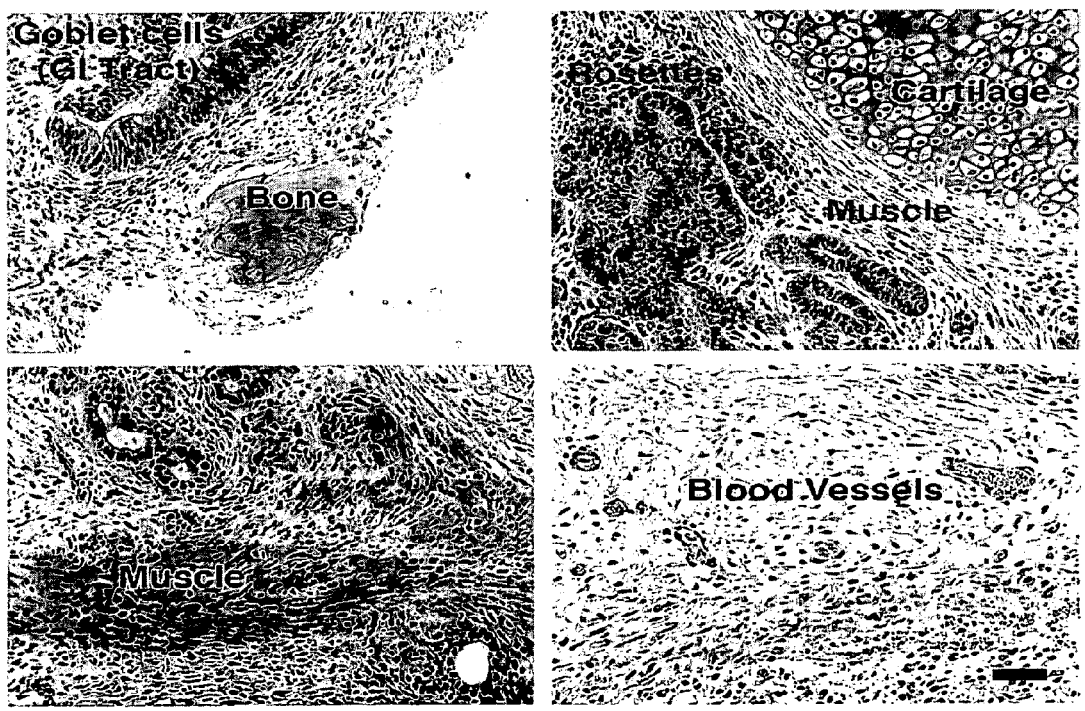
(FIG. 2j) Hematoxylin and eosin staining of teratoma sections generated from integration-free iPSC lines showing differentiation in the three germ layers: goblet cells in gastro-intestinal (GI) tract (endoderm); neural rosettes (ectoderm) and blood vessels, muscle and cartilage/bone (mesoderm). Bar=150 µm.
Figure 7:
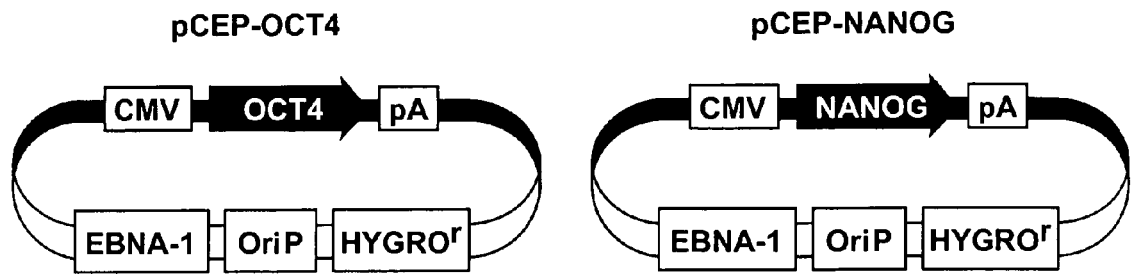
FIG. 7: Scheme of the episomal vectors used for integration-free iPSC generation. The Oct4 and Nanog cDNAs were independently cloned under the strong cytomegalovirus (CMV) promoter. EBNA-1: Epstein-Barr associated Nuclear Antigen 1 gene; OriP: the cis-DNA element oriP; Hygro$^r$: hygromycin resistant cassette; pA: polyadenylation signal.
Figure 8A:
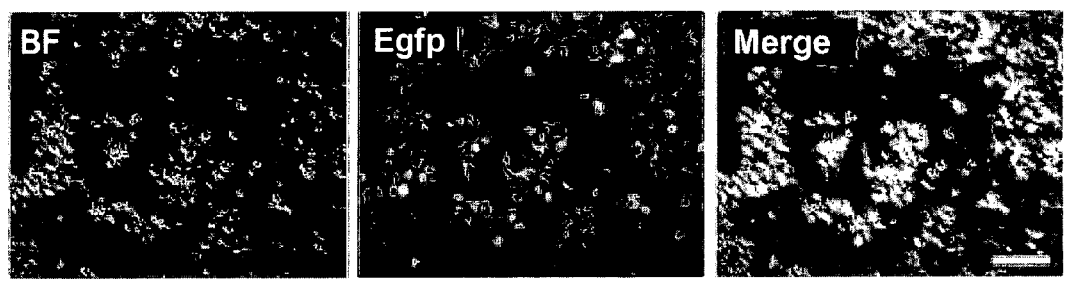
(FIG. 8a) Human fetal NSCs were electroporated with an episomal plasmid carrying the EGFP reporter gene. Transfection efficiency was around 95%.
Figure 8B:
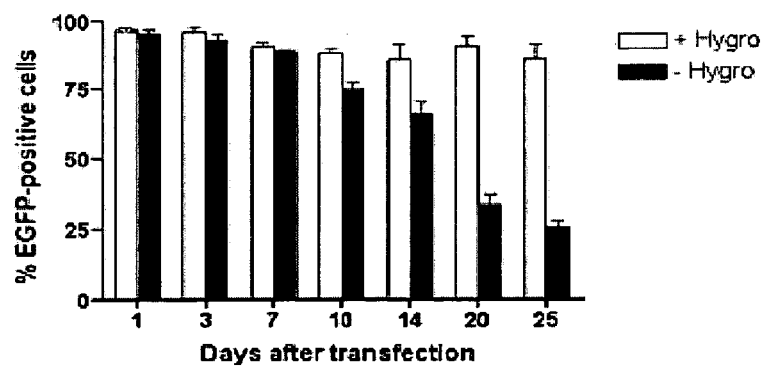
(FIG. 8b) Percentage of cells expressing EGFP in the presence or absence of hygromycin. Bar=150 µm.

To generate human iPSCs without the use of viral delivery vectors, the Oct4 and Nanog cDNAs were independently cloned under the CMV promoter into a plasmid (pCEP) with the trans-acting Epstein-Barr associated nuclear antigen 1 (EBNA-1) gene and the cis-DNA element oriP. The combination of EBNA-1 and oriP elements allows for a transient extra-chromosomal (episomal) state, avoiding genetic integration in human and non-human primate cells (Margolskee, R. F., *Curr Top Microbiol Immunol*, 158:67-95 (1992); Van Craenenbroeck, K. et al., *Gene*, 253:293-301 (2000); Van Craenenbroeck, K. et al., *Eur J Biochem*, 267:5665-5678 (2000); Leight, E. R. & Sugden, B., *Reviews in medical virology*, 10:83-100 (2000); Leight, E. R. & Sugden, B., *Mol Cell Biol*, 21:4149-4161 (2001)). The constructs also contain a mammalian selection marker (the hygromycin resistant gene) (FIG. 7). Human NSCs were electroporated with equimolar concentrations of the two episomal plasmids (pCEP-Oct4 and pCEP-Nanog) or the EGFP-reporter plasmid and plated on MEFs under hESCs conditions (FIG. 2a). Previous data in the literature suggested that reprogramming factors should be maintained for up to 12 days during iPSC generation from mouse cells (Brambrink, T. et al., *Cell stem cell*, 2:151-159 (2008); Stadtfeld, M. et al., *Cell stem cell*, 2:230-240 (2008)). Hygromycin selection was maintained for only a week, but transgene expression from the plasmid carrying the EGFP reporter gene suggested that the plasmid remained in the cells for another week before being eliminated (FIG. 8b). After 10-12 days, small iPSC colonies were first noted. Colonies were mechanically isolated and propagated under hESCs conditions on matrigel. At this point, some colonies seemed unstable, with a strong tendency to spontaneously differentiate and form a heterogeneous population of cells (FIGS. 2b-c). Undifferentiated cells were manually selected from differentiated cells according to morphology until a homogeneous population of iPSCs was achieved (FIG. 2d). These integration-free iPSC colonies were morphologically indistinguishable from hESCs, forming tight colonies of cells with a large ratio of nuclear to cytoplasm and prominent nucleoli (FIGS. 2d-e), and they did not display the NSCs' original cell morphology (FIG. 2f). The efficiency was higher (0.1-1%) when compared to fibroblasts reprogrammed with retroviruses. Several cell lineages were established from three independent transfection experiments, and three were chosen (iPSC1, iPSC2, iPSC3) for further characterization. These integration-free iPSC colonies expressed several pluripotent markers and were able to form embryoid bodies (EBs) in vitro (FIGS. 2g-h). They were also able to differentiate into representative cell types of the three germ layers, suggesting that they re-established pluripotency at the molecular and cellular levels (FIG. 2i). PCR fingerprinting confirmed their derivation from NSCs rather than from a contaminating hESC line (FIG. 9). Plasmid transfection may lead to random integration into the genome at low frequency. To test for genomic integration of plasmid DNA, several sets of PCR primers were designed to amplify various parts of the vector and transgenes (FIGS. 3a-b). Teratomas containing derivatives from all three embryonic germ layers confirmed that the integration-free hiPSCs (but not the original NPCs used) were pluripotent and able to differentiate to complex tissues in two different experimental settings (FIG. 2j and FIG. 10) Additionally, Southern blot analyses did not detect integration of plasmids in these clones (FIG. 3c). Using both methods, DNA from the transfected plasmids was not detected in any established colony, indicating a lack of genomic insertion and suggesting that the episomal vectors had been diluted from the cells over time.

Figure 12:
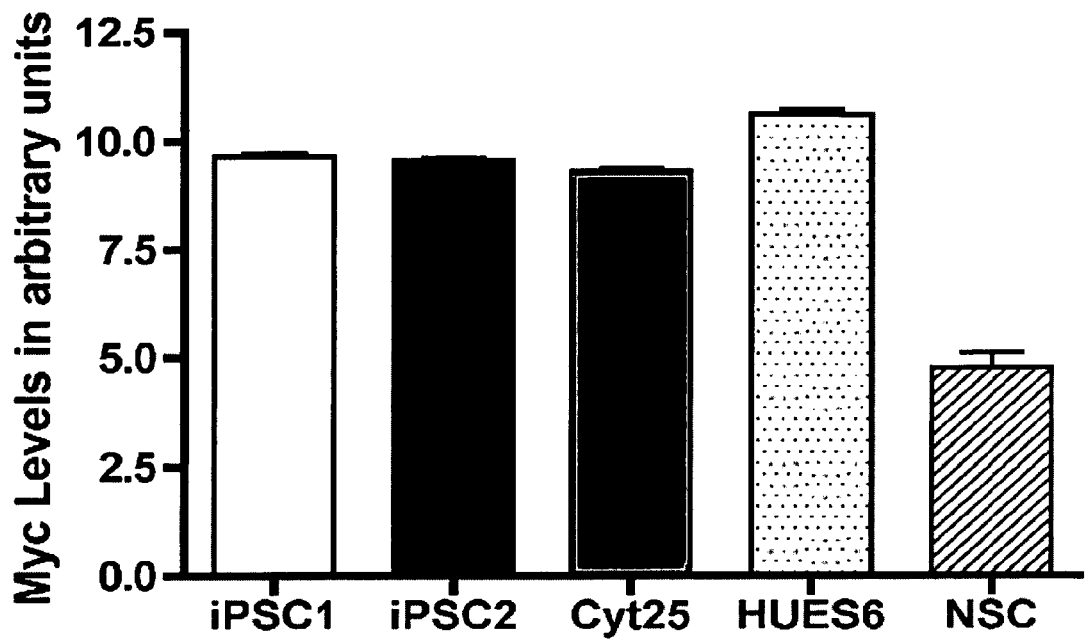
FIG. 12.

Studies were conducted to determine whether myc levels from these iPSCs derived from NSCs would change after reprogramming. Interestingly, despite the fact that the NSCs were immortalized with ectoptic expression of myc, the transcriptional activity of myc is higher in iPSCs compared to NSCs. Moreover, iPSCs clones have similar myc transcriptional levels to hESCs. See FIG. 12. Together, these observations indicate that the myc expression will likely not interfere with the global transcription profile on the iPSCs.

Figure 4A:
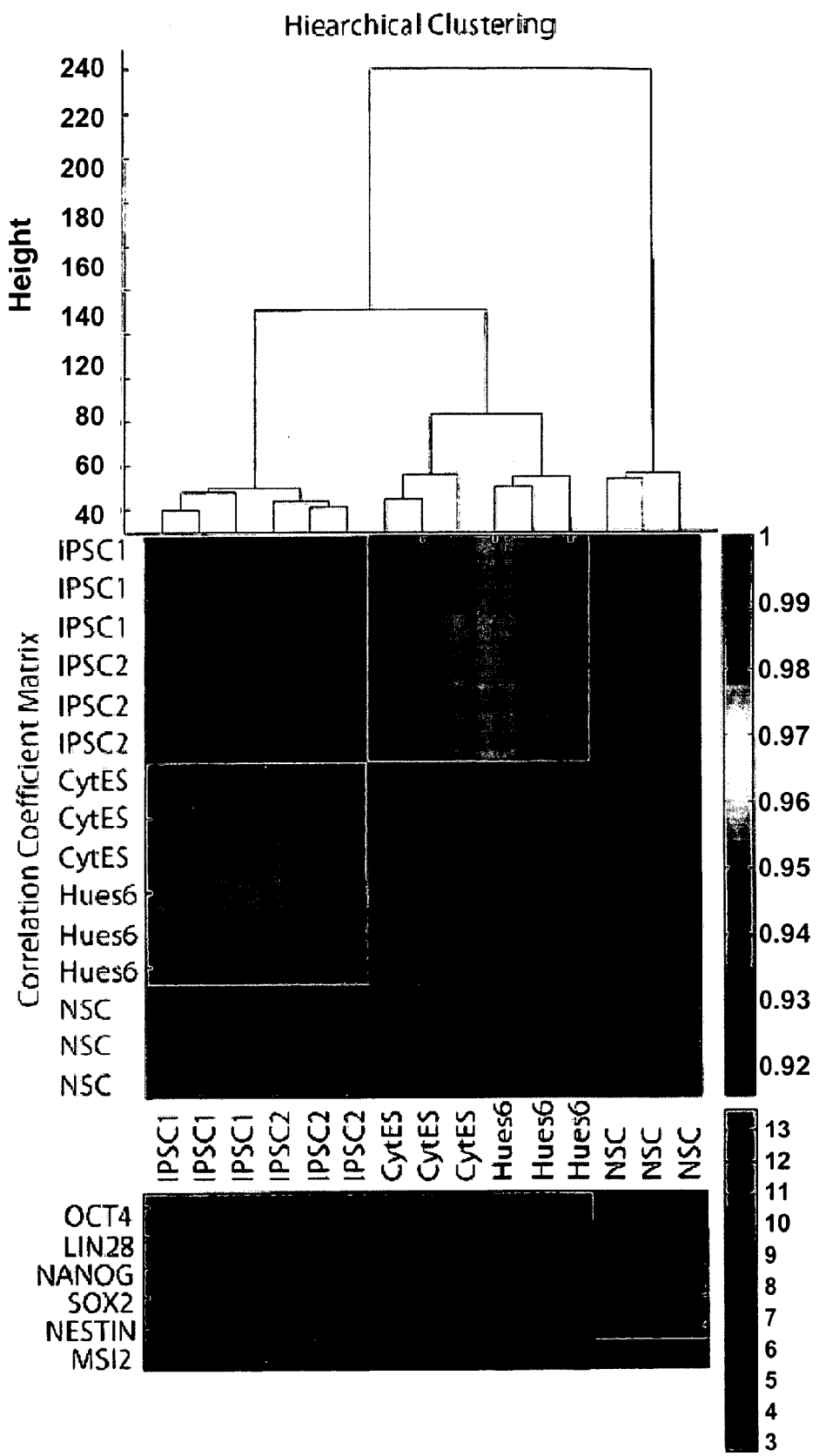
(FIG. 4a) Hierarchical clustering and correlation coefficients of microarray profiles of triplicate iPSC1, iPSC2, CytES (Cyt25 hESC), Hues6 and NSC. Panel below illustrates marker genes implicated in pluripotency of NSCs, with reporting of log 2 normalized expression values.

Next it was asked if the global molecular signatures of two integration-free iPSC lines (iPSC1, iPSC2) resembled that of available hESC lines, namely HUES6 and Cyt25. Gene expression profiles measured using Affymetrix 3' Gene-Chip® arrays were grouped by hierarchical clustering, and correlation coefficients were computed for all pair-wise comparisons (FIG. 4a). It was observed that the two iPSC lines were almost indistinguishable from each other; and that the two hESC lines were also highly similar to each other. Clearly, the iPSC and hESC lines were globally more similar to each other than to the NSC line (FIG. 4a), and combined with manual inspection of the gene expression of several known pluripotent (Oct4, LIN28, Sox2, Nestin, Nanog) and neural stem cell markers (Sox2, Nestin and Musashi2) as measured on the arrays, it was concluded that the reprogramming was successful (FIG. 4a).

Figure 4B:
(FIG. 4b) Refseq-annotated genes that were insufficiently induced in iPSCs relative to hESCs.
Figure 4C:
(FIG. 4c) Refseq-annotated genes that were insufficiently silenced in iPSCs relative to hESCs.
Figure 10:
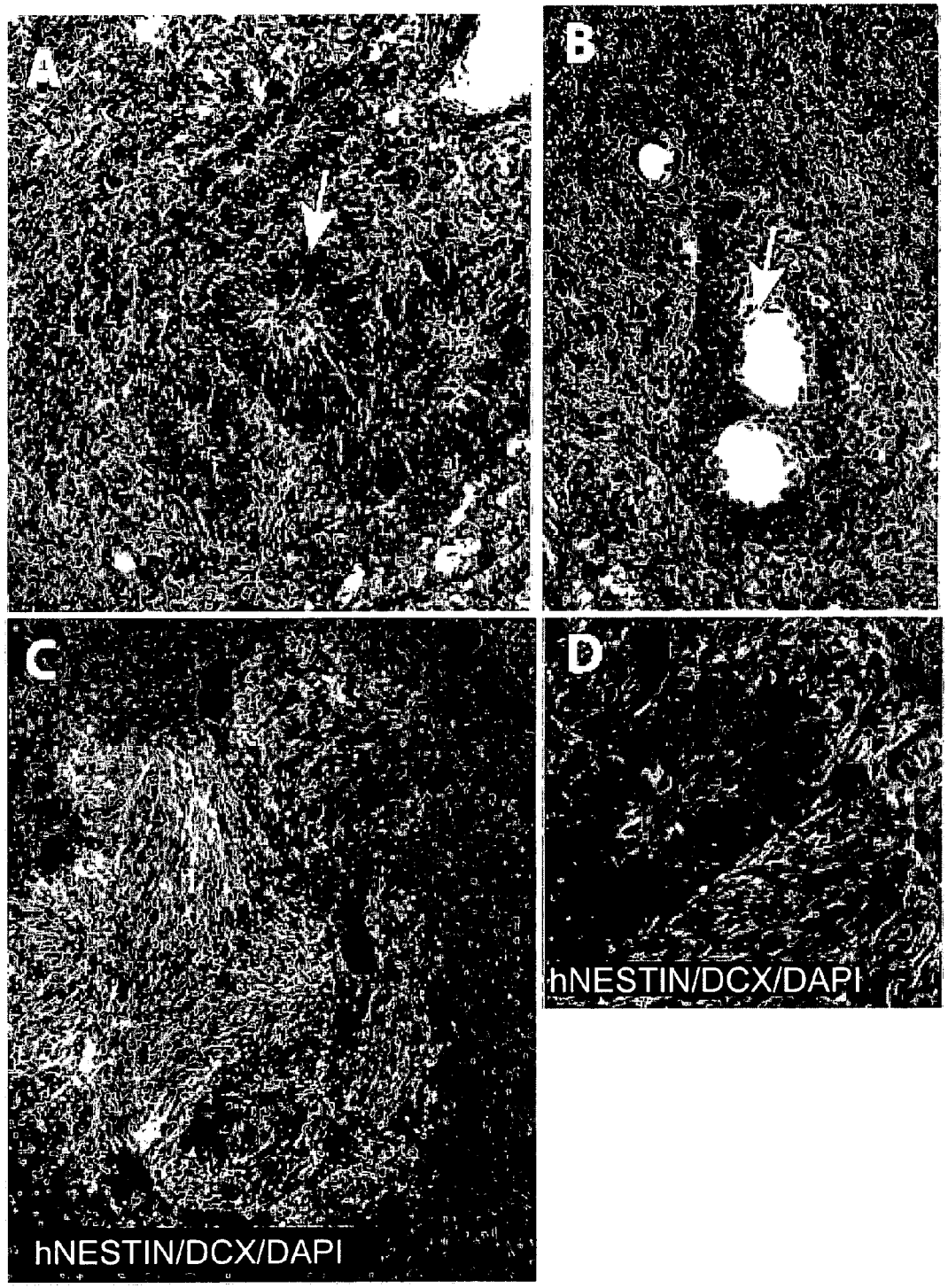
FIG. 10: Development of teratomas after spinal cord injections of iPSCs into lumbar gray matter. Lumbar spinal cord sections were stained with H&E at 3 weeks after grafting (FIGS. 10a-b). The presence of rosette-like structures (FIG. 10a, arrow) and ectoderm-derived squamous epithelium was identified (FIG. 10b, arrow).

Despite the global similarity between iPSCs and hESCs, the profiles were not completely indistinguishable, which led to the study of the molecular differences. Four independent (A versus B) group-wise comparisons were performed to identify differentially expressed genes: (i) iPSC versus hESC (1,952 Refseq-annotated genes were significantly enriched in iPSCs versus hESCs; 1,072 genes were enriched in hESCs versus iPSCs at P<0.01 after correcting for multiple hypotheses testing); (ii) iPSC versus NSC (3,347 genes were significantly enriched in iPSCs versus NSCs; 2,959 genes were enriched in NSCs versus iPSCs); (iii) hESC versus NSC (2,376 genes were significantly enriched in hESCs versus NSCs; 2,541 genes were enriched in NSCs versus hESCs); (iv) iPSC and hESC versus NSC (3,730 genes were significantly enriched in iPSCs and hESCs, versus NSCs and 3,638 genes were enriched in NSCs versus iPSCs and hESCs. The term "Refseq" as customarily used in the art refers to accession numbers from the NCBI (National Center for Biotechnology Information) database. Restricting these differentially expressed genes to ones that changed by at least 4-fold in any comparison, at a stringent p-value cutoff of P<0.0001, three groups of biologically interesting genes were identified. The first group of iPSC-expressed genes was not sufficiently induced to comparable levels as in hESCs and was still at similar levels to NSCs (FIG. 4b). This group contained factors that were important in early embryonic fate, such as Stella, ZFP42, CLDN10, LEFTY1 and LEFTY2. The second group contained iPSC-expressed genes that were not sufficiently silenced, such as ZIC1, OLIG2, EN2 and PTX3, which were associated with the neuronal lineage (FIG. 4c). The third group consisted of genes that were upregulated in iPSCs, which were silenced in both NSCs and hESCs, suggesting that these genes were important downstream factors in the reprogramming step to induce pluripotent cells (FIG. 10). Overall, the transcriptome analyses indicated that, whereas the IPSCs are globally similar to hESCs, they are not indistinguishable, primarily due to the insufficient suppression or induction of NSC-specific or early embryonic-specific genes, respectively, as well as a class of genes that were upregulated during the reprogramming step.

Figure 5A:
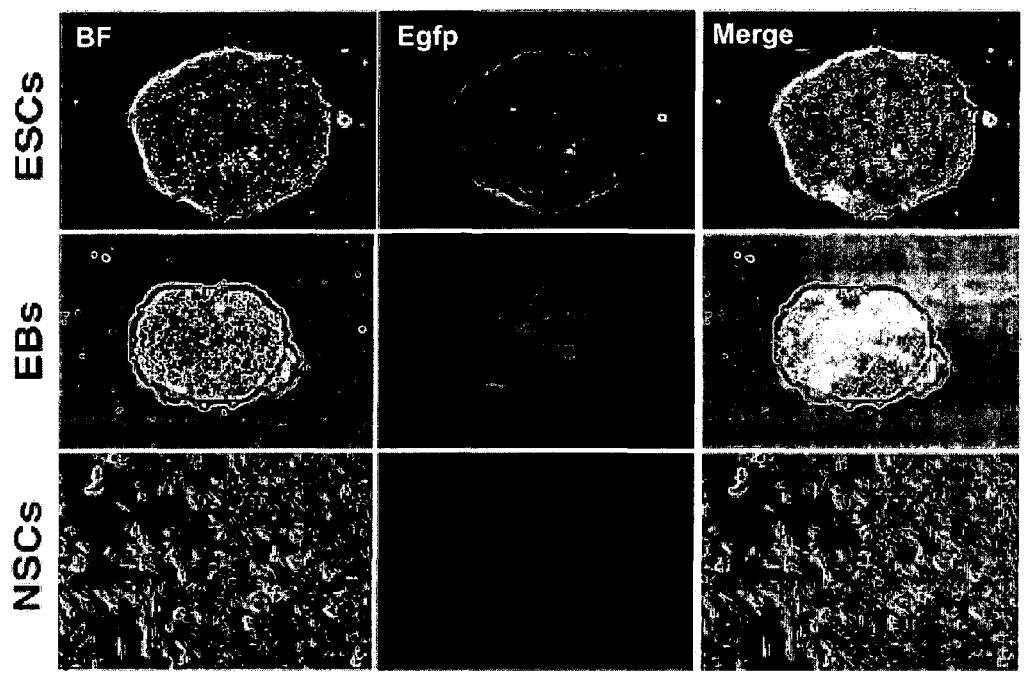
(FIG. 5a) Undifferentiated H1 Oct4-EGFP hESCs line expresses the EGFP reporter gene that is gradually turned off during NSC differentiation. NSCs are morphologically distinct from hESCs.
Figure 5B:
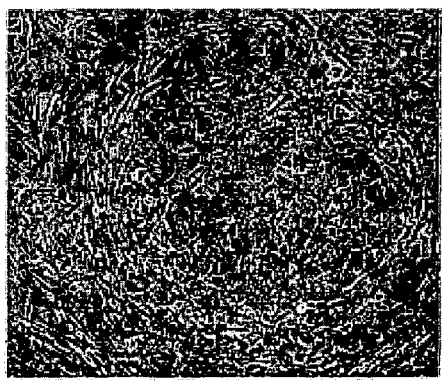
(FIG. 5b) Small iPSC colonies can be detected 10 days after transfection with pCEP-Oct4 and pCEP-Nanog.
Figure 5C:
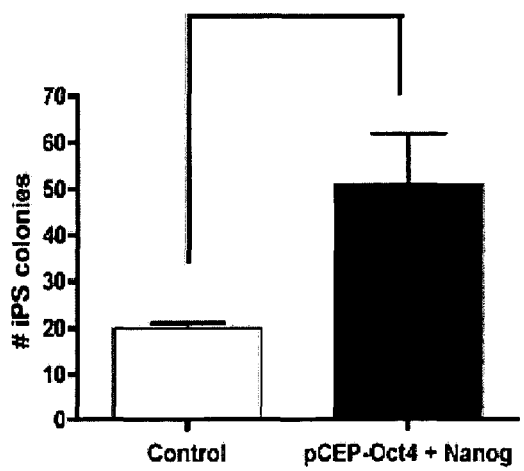
(FIG. 5c) Typical number of iPSC colonies obtained with electroporation of pCEP-Oct4 and Nanog or with a control plasmid. Bar=150 µm.

Next, the transient transfection was repeated using primary NSCs derived from the H1 hESC line that contain the EGFP reporter cassette knocked in the endogenous Oct4 gene by homologous recombination (Zwaka, T. P. & Thomson, J. A., *Nat Biotechnol,* 21:319-321 (2003)). The H1-Oct4-EGFP cell line expressed EGFP, which turned off during differentiation (FIG. 5a). NSCs were generated using our previous established protocol and consisted of a cell population with a genetic profile distinct from both human fetal cells and hESCs (Cezar, G. G. et al., *Stem Cells and Development,* 16:869-882 (2007); Yeo, G. W. et al., *PLoS Computational Biology,* 3:1951-1967 (2007)). NSCs derived from the H1-EGFP do not express EGFP (FIG. 5a). An EGFP-negative population of NSCs was electroporated with both episomal plasmids carrying Oct4 and Nanog. Several iPSC colonies were observed as early as 10 days after transfection, becoming morphologically indistinguishable from the original H1-Oct4-EGFP cell line (FIGS. 5b-c). As a control, the same cell population were electroporated with Oct4 only. Interestingly, we detected several colonies when cells were transfected with Oct4 alone. These colonies were positive for pluripotent makers, such as Nanog and Lin28, suggesting efficient reprogramming. The efficiency was 10-fold lower when compared to human fetal NSCs, which could be due to the fact that fetal NSCs have a genetic profile closer to hESCs when compared to hESC-derived NSCs. Alternatively, the high efficiency obtained with fetal NSCs could be due to the c-Myc transgene used for the immortalization process.

Figure 6:
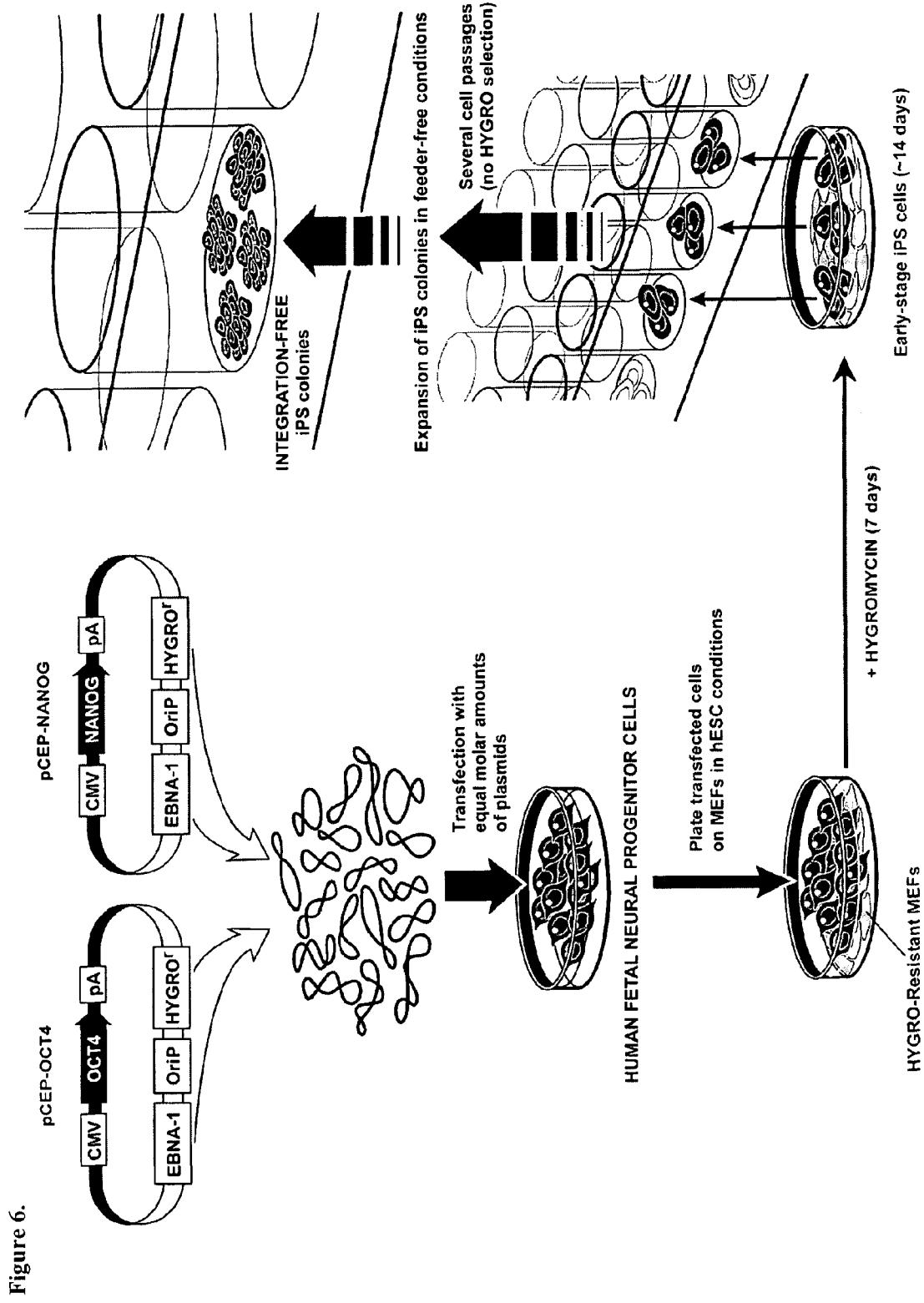
FIG. 6: Schematic model of integration-free human iPSC generation from NSCs. Episomal plasmids carrying reprogramming factors are transfected into NSCs and cells are plated on MEFs. On the following day, medium is changed to the hESC condition. Resistant selection is kept for a week. After 14 days, iPSC colonies are visible and could be transferred to a feeder-free condition. Individual colonies are expanded and ready for characterization. At this time, no evidence of plasmid integration is found.

In conclusion, using a simple methodology (FIG. 6), it was demonstrated that it is possible to generate human iPSCs at a high frequency without viruses and with no evidence of genetic insertion into cell chromosomes. Human iPSCs were achieved using transient episomal vectors carrying the cDNAs for Oct4 and Nanog in a cell type that was likely more prone to genetic reprogramming, such as NSCs. It was also demonstrated here for the first time that a immortalized cell line can be successfully reprogrammed. The c-Myc-immortalized NSCs represent a reliable tool to dissect individual factors required for reprogramming. On the other hand, the data from hESC-derived NSCs indicates that reprogramming can be achieved without ectopic expression of the tumor-associated genes, c-Myc and Klf4. Human iPSCs generated without virus or genomic integration were then used to assess whether human iPSCs and ESCs are really equivalent at the molecular and functional levels, avoiding eventual interference from transgene expression in iPSCs that may affect their genetic signature, differentiation behavior or developmental potential.

The results support earlier observations that viral integration is dispensable for genetic reprogramming (Aoi, T. et al., *Science*, 321:699-702 (2008); Varas, F. et al., *Stem Cells* (2008)). The data point to the fact that viral integration does not facilitate iPSC generation, and the efficiency is probably due to the duration and level of the transgenes achieved with episomal plasmids. It was estimated that each cell contains as many as 50 copies of each episomal plasmid in the nucleus (Belt, P. B. et al., *Gene*, 84:407-417 (1989)). After a critical amount of time, selection is removed and the episomal vectors are eliminated from the cells during duplication. Although episomal plasmids were never detected in iPSC established colonies, eventual leftover plasmid will likely be severely methylated when cells reach a pluripotent state, avoiding excess transgene expression after reprogramming (Kameda, T. et al., *Biochem Biophys Res Commun*, 349:1269-1277 (2006)). In such a system, the amount and time of gene expression can be easily controlled. It can be anticipated that different cell types will require a distinct cocktail of pluripotent factors, under specific timing and expression conditions. It remains to be determined if the proposed method can be applied to adult somatic cells. Finally, the strategy described here is a valuable tool for creating safer patient-specific cells and thus could have major implications for a future cell therapy.

VI. Materials and Methods

Cell Culture

Human fetal NSCs (ReNCell® VM, Chemicon) were culture on laminin-coated dishes, in ReNCell® maintenance medium (Chemicon) in the presence of basic fibroblast growth factor 2 (bFGF2), following the manufacturer's instruction. The hESC Cyt25 (Cythera, San Diego) and HEUS6 cell lines were cultured as previously described (Muotri, A. R. et al., *Proc Natl Acad Sci USA*, 102:18644-18648 (2005)). Two days after infection/transfection, cells were plated on mitotically irradiated MEFs (Chemicon), with hESCs medium, in the presence or not of 50 µg/ml of hygromycin B (Invitrogen). After 2 weeks, iPSC colonies were directly transferred to feeder-free conditions, on matrigel-coated dishes (BD) using mTeSR™1 (StemCell Technologies). Established iPSC colonies were kept in feeder-free conditions indefinitely and passed using mechanical dissociation. EBs were formed by mechanical dissociation of cell clusters and plating into low-adherence dishes in hESC medium without bFGF2 for seven days.

Lentiviral and Episomal Plasmids

Lentiviral vectors containing the Oct4 and Nanog human cDNAs from Yamanaka's group were obtained from Addgene. The cDNAs were then subcloned into the pCEP4β episomal plasmid (Invitrogen). Plasmid transfections were done by electroporation of equimolar amounts of pCEP-Oct4 and pCEP-Nanog (5 µg each) using the nucleofactor for rat NSCs, following the manufacturer's instructions (Amaxa Biosystem). Lentiviruses were produced by triple transfection of HEK293T cells followed by ultracentrifugation as previously described elsewhere (Muotri, A. R. et al., *Proc Natl Acad Sci USA*, 102:18644-18648 (2005)). Fetal NSCs were infected with both Lenti-Oct4 and Lenti-Nanog at a titer of $0.5 \times 10^{10}$ gene transfer units/ml overnight, followed by a 2-day recovery period before being plated on mitotically inactive MEFs.

Immunocytochemistry

Cells were briefly fixed in 4% paraformaldehyde and then permeabilized with 0.5% Triton®-X in PBS. Cells were blocked in 0.5% Triton®-X with 5% donkey serum for 1 hour before incubation with primary antibody overnight at 4° C. After 3 washes in PBS, cells were incubated with secondary antibodies (Jackson ImmunoResearch) for 2 hours at room temperature. Fluorescent signals were detected using a Zeiss inverted microscope and images were processed with Photoshop® CS3 (Adobe Systems). Primary antibodies used in this study are SSEA-4, TRA-1-60, TRA-1-81 (1:100, Chemicon) and Lin28 (1:500 R&D Systems). Alkaline phosphatase activity was detected in live cells using the Vector® Red Alkaline Phosphatase substrate kit (Vector Laboratories).

Genomic PCR and Southern Blot

Genomic DNA was isolated and prepared using standard molecular techniques. The PCR primers were designed to recognize the pCEP4 episomal vector (Invitrogen). The primers pairs used to amplify the plasmid back bone follow: CEP19-F: 5'-tatgatgacacaaaccccgcccag-3' (SEQ ID NO:1) and CEP19-R: 5'-aaagcacgagattcttcgccctcc-3' (SEQ ID NO:2); CEP20-F: 5'-gaaaaagcctgaactcaccgc-3' (SEQ ID NO:3) and CEP20-R: 5'-aaagcacgagattcttcgccctcc-3' (SEQ ID NO:4); CEP21-F: 5'-ggcgaagaatctcgtgctttc-3' (SEQ ID NO:5) and CEP21-R: 5'-cggtgtcgtccatcacagtttg-3' (SEQ ID NO:6); CEP22-F: 5'-cgcaaggaatcggtcaatacactac-3 (SEQ ID NO:7) and CEP22-R: 5'-tccatacaagccaaccacgg-3' (SEQ ID NO:8); CEP23-F: 5'-ggatttcggctccaacaatgtc-3' (SEQ ID NO:9) and CEP23-R: 5'-tgaacaaacgacccaacaccc-3' (SEQ ID NO:10). The primers used to amplify the transgene only follow: CEP1-F1: 5'-gcgtggatagcggtttgactc-3' (SEQ ID NO:11); Oct4R1: 5'-aaatccgaagccaggtgtc-3' (SEQ ID NO:12); NanogR1: 5'-cagtcggatgcttcaaag-3' (SEQ ID NO:13). Southern blot with 10 µg of genomic DNA, previously digested with BamHI, was performed using standard molecular techniques. The probe used was a fragment of pCEP4 plasmid cut with NruI and SalI enzymes. As customary in the art, in the context of primer nomenclature the terms "F," "F1," "Fw" and the like refer to forward primers, and the terms "R," "R1," "Rv" and the like refer to reverse primers.

RNA Extraction and RT-PCR

Total cellular RNA was extracted from ~5×10⁶ cells using the RNeasy Protect Mini kit (Qiagen, Valencia, Calif.), according to the manufacturer's instructions, and reverse transcribed using the SuperScript® III First-Strand Synthesis System RT-PCR from Invitrogen. The cDNA was amplified by PCR using Accuprime™ Taq DNA polymerase system (Invitrogen). The primer sequences follow: hNanog-Fw: 5' cctatgcctgtgatttgtgg 3' (SEQ ID NO:14) and hNanog-Rv: 5' ctgggaccttgtcttcctt 3' (SEQ ID NO:15); hBRACHYURY-F: 5' gccctctccctccctccacgcacag 3' (SEQ ID NO:16) and hBRACHYURY-R: 5' cggcgccgttgctcacagaccacagg 3' (SEQ ID NO:17); hKRT-18-F: tctgtggagaacgacatcca (SEQ ID NO:18) and KRT-18-R: 5' ctgtacgtctcagctctgtga 3' (SEQ ID NO:19); h-AFP-F: 5' aaaagcccactccagcatc 3' (SEQ ID NO:20) and AFP-R: 5' cagacaatccagcacatctc 3' (SEQ ID NO:21); GATA-4-F: 5' ctccttcaggcagtgagagc 3' (SEQ ID NO:22) and GATA-4-R: 5' gagatgcagtgtgctcgtgc 3' (SEQ ID NO:23); hGAPDH-Fw: 5' accacagtccatgccatcac 3' (SEQ ID NO:24), hGAPDH-Rv: 5' tccaccaccctgttgctgta 3' (SEQ ID NO:25). PCR products were separated by electrophoresis on a 2% agarose gel, stained with ethidium bromide and visualized by UV illumination.

Teratoma Formation in Nude Mice

Around 1-3×10⁶ cells were injected into the dorsal flanks of nude mice (CByJ.Cg-Foxn1nu/J) anesthetized with isoflurane. Five to 6 weeks after injection, teratomas were dissected, fixed overnight in 10% buffered formalin phosphate and embedded in paraffin. Sections were stained with hematoxylin and eosin for further analysis.

In Vivo Spinal iPSCs Grafting and Identification of Teratomas

Adult Sprague-Dawley male rats (320-350 g; n=6) were anesthetized with isoflurane (1.5-2% maintenance, in room air), placed into a spinal unit apparatus (Stoelting, Wood Dale, Ill., USA) and a partial Th12-L1 laminectomy was performed using a dental drill (exposing the dorsal surface of L2-L5 segments). Using a glass capillary (tip diameter 80-100 µm) connected to a microinjector (Kopf Instruments, Tujunga, Calif.), rats were injected with 0.5 µl (10, 100 cells per injection) of the iPS (n=3) or proliferating H9 cells in DMEF/F12 media. The duration of each injection was 60 s followed by 30 s pause before capillary withdrawal. The center of the injection was targeted into the dorsal horn (distance from the dorsal surface of the spinal cord at L3 level: 0.5-0.7 m). Ten injections (500-800 µm rostrocaudally apart) were made on each side of the lumbar spinal cord. After injections, the incision was cleaned with penicillin-streptomycin solution and sutured in two layers. Three or four weeks after cell grafting, rats were deeply anesthetized with pentobarbital and phenytoin and transcardially perfused with 200 ml heparinized saline followed by 250 ml of 4% paraformaldehyde in PBS. The spinal cords were dissected and postfixed in 4% formaldehyde in PBS overnight at 4° C. and then cryoprotected in 30% sucrose PBS until transverse sections (30 µm thick) were cut in a cryostat and mounted on Silane-Prep slides (Sigma). Sections were stained with H&E or immunostained overnight at 4° C. with primary human specific (h) or non-specific antibodies diluted in PBS with 0.2% Triton® X-100: mouse anti-nuclear matrix protein/h-nuc (hNUMA; 1:100; Millipore, Temecula, Calif., USA); goat anti-doublecortin (DCX; 1:1000; Millipore); mouse anti-Nestin (hNestin; Chemicon). After incubation with primary antibodies, sections were washed 3× in PBS and incubated with fluorescent-conjugated secondary donkey anti-mouse, or donkey anti-goat antibodies (Alex 488, 546; 1:250; Invitrogen Corp., Carlsbad, Calif., USA) and DAPI for general nuclear staining. Sections were then dried at room temperature, covered with Prolong™ anti-fade kit (Invitrogen Corp., Carlsbad, Calif., USA) and analyzed with confocal microscopy (Olympus, Fluoview™1000).

DNA Fingerprinting

DNA fingerprinting analysis was performed by Cell Line Genetics (Madison, Wis.).

Microarray Analysis

The Affymetrix Power Tools (APT) suite of programs and Affymetrix HG-U133 Plus 2.0 library files and annotation were obtained from the Affymetrix support website. Gene-level signal estimates were derived from the CEL files by RMA-sketch normalization as a method in the apt-probeset-summarize program. Hierarchical clustering of the full dataset of 15 (2 hiPSC lines samples, 2 hESC lines, 1 NSC line in triplicate each) by 54,675 probeset values was performed by complete linkage using Euclidean distance as a similarity metric in Matlab. The t-statistic $t_{A,B}=(m_A-m_B)/\text{sqrt}(((n_A-1)s^2_A+(n_B-1)s^2_B)\ (n_A+n_B))/((n_An_B)\ (nA+n_B-2)))$, where $n_A$ and $n_B$ were the number of replicates, $m_A$ and $m_B$ were the mean, and $s^2A$ and $s^2_B$ were the variances of the expression values for the two datasets was calculated representing the differential enrichment of a gene using gene-level estimates in cell-type(s) A relative to cell-type(s) B. Multiple hypothesis testing was corrected by controlling for the false discovery rate (Benjamini-Hochberg). Four independent (A versus B) comparisons were performed to identify differentially expressed genes: (i) iPSCs versus hESCs; (ii) iPSCs versus NSCs; (iii) hESCs versus NSCs; and (iv) iPSCs and hESCs versus NSCs. A total of 653 probesets were retained at a stringent cutoff of p<0.0001 and fold-change of 4. Probesets were centered by mean expression values, and hierarchical clustering was performed by complete linkage and uncentered correlation as the similarity metric using Cluster 3.0 program. Results were visualized using Java Treeview. Gene ontology analysis was performed as described in Yeo et al., 2005 (Yeo, G. W. et al., *Proc Natl Acad Sci USA*, 102:2850-2855 (2005)).

VII. REFERENCES

References cited to herein include the following: Takahashi, K. & Yamanaka, S, *Cell* 126, 663-676 (2006); Takahashi, K. et al., *Cell* 131, 861-872 (2007); Yu, J. et al., *Science* 318, 1917-1920 (2007); Lowry, W. E. et al., *Proc Natl Acad Sci USA* 105, 2883-2888 (2008); Park, I. H. et al., *Nature protocols* 3, 1180-1186 (2008); Kustikova, O. et al., *Science* 308, 1171-1174 (2005); Best, S. M., *Annu Rev Microbiol* 62, 171-192 (2008); Nakagawa, M. et al., *Nat Biotechnol* 26, 101-106 (2008); Stadtfeld, M. et al., *Science* 322, 945-949 (2008); Okita, K. et al., *Science* 322, 949-953 (2008); Aasen, T. et al., *Nat Biotechnol* (2008); Eminli, S. et al., *Stem Cells* 26, 2467-2474 (2008); Kim, J. B. et al., *Nature* 454, 646-650 (2008); Aoi, T. et al., *Science* 321, 699-702 (2008); Hanna, J. et al., *Cell* 133, 250-264 (2008); Silva, J. et al., *PLoS Biol* 6, e253 (2008); Okita, K., Ichisaka, T. & Yamanaka, S., *Nature* 448, 313-317 (2007); Wernig, M., Meissner, A., Cassady, J. P. & Jaenisch, R., *Cell stem cell* 2, 10-12 (2008); Breier, J. M., Radio, N. M., Mundy, W. R. & Shafer, T. J., *Toxicol Sci* 105, 119-133 (2008); Donato, R. et al., *BMC neuroscience* 8, 36 (2007); Muotri, A. R. et al., *Proc Natl Acad Sci USA* 102, 18644-18648 (2005); Margolskee, R. F., *Curr Top Microbiol Immunol* 158, 67-95 (1992); Van Craenenbroeck, K., Vanhoenacker, P., Duchau, H. & Haegeman, G., *Gene* 253, 293-301 (2000); Van Craenenbroeck, K., Vanhoenacker, P. & Haegeman, G., *Eur J Biochem* 267, 5665-5678 (2000); Leight, E. R. & Sugden, B., *Reviews in medical virology* 10, 83-100 (2000); Leight, E. R. & Sugden, B., *Mol Cell Biol* 21, 4149-4161 (2001); Brambrink, T. et al., *Cell stem cell* 2, 151-159 (2008); Stadtfeld, M., Maherali, N., Breault, D. T. & Hochedlinger, K., *Cell stem cell* 2, 230-240 (2008); Zwaka, T. P. & Thomson, J. A., *Nat Biotechnol* 21, 319-321 (2003); Cezar, G. G. et al., *Stem cells and development* 16, 869-882 (2007); Yeo, G. W. et al., *PLoS computational biology* 3, 1951-1967 (2007); Varas, F. et al., *Stem Cells* (2008); Belt, P. B. et al., *Gene* 84, 407-417 (1989); Kameda, T., Smuga-Otto, K. & Thomson, J. A., *Biochem Biophys Res Commun* 349, 1269-1277 (2006); Yeo, G. W. et al., *Proc Natl Acad Sci USA* 102, 2850-2855 (2005); Kaji, K. et al., *Nature* (2009); Woltjen, K. et al., *Nature* (2009).

VIII. Informal Sequence Listing

| Descriptor | Sequence | SEQ ID NO |
|---|---|---|
| CEP19-F | 5'- tatgatgacacaaacccgcccag -3' | 1 |
| CEP19-R | 5'- aaagcacgagattcttcgccctcc -3' | 2 |
| CEP20-F | 5'- gaaaaagcctgaactcaccgc -3' | 3 |
| CEP20-R | 5'- aaagcacgagattcttcgccctcc -3' | 4 |

| Descriptor | Sequence | SEQ ID NO |
|---|---|---|
| CEP21-F | 5'- ggcgaagaatctcgtgctttc -3' | 5 |
| CEP21-R | 5'- cggtgtcgtccatcacagtttg -3' | 6 |
| CEP22-F | 5'- cgcaaggaatcggtcaatacactac -3 | 7 |
| CEP22-R | 5'- tccatacaagccaaccacgg -3' | 8 |
| CEP23-F | 5'- ggatttcggctccaacaatgtc -3' | 9 |
| CEP23-R | 5'- tgaacaaacgacccaacaccc -3' | 10 |
| CEP1-F1 | 5'- gcgtggatagcggtttgactc -3' | 11 |
| Oct4R1 | 5'- aaatccgaagccaggtgtc -3' | 12 |
| NanogR1 | 5'- cagtcggatgcttcaaag -3' | 13 |
| hNanog-Fw | 5' cctatgcctgtgatttgtgg 3' | 14 |
| hNanog-Rv | 5' ctgggaccttgtcttcctttt 3' | 15 |
| hBRACHYURY-F | 5' gccctctccctcccctccacgcacag 3' | 16 |
| hBRACHYURY-R | 5' cggcgccgttgctcacagaccacagg 3' | 17 |
| hKRT-18-F | tctgtggagaacgacatcca | 18 |
| KRT-18-R | 5' ctgtacgtctcagctctgtga 3' | 19 |
| h-AFP-F | 5' aaaagcccactccagcatc 3' | 20 |
| AFP-R | 5' cagacaatccagcacatctc 3' | 221 |
| GATA-4-F | 5' ctccttcaggcagtgagagc 3' | 22 |
| GATA-4-R | 5' gagatgcagtgtgctcgtgc 3' | 23 |
| hGAPDH-Fw | 5' accacagtccatgccatcac 3' | 24 |
| hGAPDH-Rv | 5' tccaccaccctgttgctgta 3' | 25 |

What is claimed is:

1. A footprint-free human induced pluripotent stem cell comprising an episomal vector comprising a nucleic acid encoding an Oct4 protein, and an episomal vector comprising a nucleic acid encoding a Nanog protein, wherein the footprint-free human induced pluripotent stem cell does not contain any detectable genomic integration of the episomal vector nucleic acid encoding the Oct4 protein or the episomal nucleic acid encoding the Nanog protein.

2. A method for preparing a footprint-free human induced pluripotent stem cell comprising:
   (i) transfecting a human neural stem cell with a nucleic acid encoding an Oct4 protein to form a transfected human neural stem cell, wherein the nucleic acid encoding the Oct4 protein is comprised in an episomal vector comprising an Epstein-Barr associated nuclear antigen 1 (EBNA-1) gene and an OriP nucleic acid sequence,
   transfecting the human neural stem cell with a nucleic acid encoding a Nanog protein, wherein the nucleic acid encoding the Nanog protein is comprised in an episomal vector comprising an Epstein-Barr associated nuclear antigen 1 (EBNA-1) gene and an OriP nucleic acid sequence,
   wherein said transfecting is performed without the use of a viral transfection system; and
   (ii) culturing the transfected human neural stem cell under embryonic stem cell conditions thereby forming said footprint-free human induced pluripotent stem cell.

3. The method of claim 2, wherein said nucleic acid encoding the Oct4 protein and said nucleic acid encoding the Nanog protein are comprised in the same episomal vector.

4. The method of claim 2, wherein said nucleic acid encoding the Oct4 protein is comprised in a first episomal vector and said nucleic acid encoding the Nanog protein is comprised in a second episomal vector.

5. The method of claim 2, wherein said human neural stem cell is not transfected with an additional nucleic acid encoding a Wye protein, a Sox2 protein, a Lin28 protein or a KLF4 protein.

6. The method of claim 2, wherein said human neural stem cell is isolated from a human embryo.

7. The method of claim 2, wherein said human neural stem cell is derived from a human embryonic stem cell.

* * * * *